United States Patent
Wallace et al.

(10) Patent No.: US 9,314,289 B2
(45) Date of Patent: Apr. 19, 2016

(54) CLEANING DEVICE AND METHODS

(75) Inventors: Michael Wallace, Pleasanton, CA (US); David S. Utley, Redwood City, CA (US); Brent Gerberding, San Jose, CA (US); Robert Garabedian, Mountain View, CA (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 13/591,991

(22) Filed: Aug. 22, 2012

(65) Prior Publication Data

US 2013/0218153 A1    Aug. 22, 2013

Related U.S. Application Data

(63) Continuation of application No. 11/830,251, filed on Jul. 30, 2007, now Pat. No. 8,273,012.

(51) Int. Cl.
| | |
|---|---|
| *A61B 1/00* | (2006.01) |
| *A61B 18/00* | (2006.01) |
| *A61B 18/04* | (2006.01) |
| *A61B 17/00* | (2006.01) |
| *A61B 17/32* | (2006.01) |

(52) U.S. Cl.
CPC ............... *A61B 18/00* (2013.01); *A61B 18/04* (2013.01); *A61B 17/00234* (2013.01); *A61B 2017/32008* (2013.01); *A61B 2017/320012* (2013.01)

(58) Field of Classification Search
CPC ..................................... A61B 18/00
USPC ................................. 600/104, 562
See application file for complete search history.

(56) References Cited

U.S. PATENT DOCUMENTS

| | | | |
|---|---|---|---|
| 552,832 | A | 1/1896 | Fort |
| 1,798,902 | A | 3/1931 | Raney |
| 3,517,128 | A | 6/1970 | Hines |
| 3,901,241 | A | 8/1975 | Allen, Jr. |
| 3,924,628 | A | 12/1975 | Droegemueller et al. |
| 4,011,872 | A | 3/1977 | Komiya |
| 4,030,503 | A | 6/1977 | Clark, III |
| 4,196,724 | A | 4/1980 | Wirt et al. |
| 4,304,239 | A | 12/1981 | Perlin |
| 4,311,154 | A | 1/1982 | Sterzer et al. |
| 4,411,266 | A | 10/1983 | Cosman |
| 4,423,812 | A | 1/1984 | Sato |
| 4,532,924 | A | 8/1985 | Auth et al. |
| 4,565,200 | A | 1/1986 | Cosman |

(Continued)

FOREIGN PATENT DOCUMENTS

| | | |
|---|---|---|
| DE | 3838840 | 5/1990 |
| DE | 4303882 | 8/1994 |

(Continued)

OTHER PUBLICATIONS

Castell, DO. O. Gastroesophageal Reflux Disease: Current Strategies for Patient Management. arch Fam. Med. 1996; 5(4):221-227.

(Continued)

*Primary Examiner* — Sean Dougherty

(57) ABSTRACT

An apparatus for treating tissue within a lumen may include a therapeutic or diagnostic instrument. A cleaning device may also be supported by the instrument. The cleaning device has a portion of a cleaning surface positioned proximal to the distal end of the cleaning device.

19 Claims, 18 Drawing Sheets

(56) References Cited

U.S. PATENT DOCUMENTS

| | | |
|---|---|---|
| 4,640,298 A | 2/1987 | Pless et al. |
| 4,658,836 A | 4/1987 | Turner |
| 4,662,383 A | 5/1987 | Sogawa et al. |
| 4,674,481 A | 6/1987 | Boddie, Jr. et al. |
| 4,676,258 A | 6/1987 | Inokuchi et al. |
| 4,705,041 A | 11/1987 | Kim |
| 4,740,207 A | 4/1988 | Kreamer |
| 4,765,331 A | 8/1988 | Petruzzi et al. |
| 4,776,349 A | 10/1988 | Nashef et al. |
| 4,794,928 A | 1/1989 | Kletschka |
| 4,860,744 A | 8/1989 | Johnson et al. |
| 4,887,614 A | 12/1989 | Shirakami et al. |
| 4,895,138 A | 1/1990 | Yabe |
| 4,901,737 A | 2/1990 | Toone |
| 4,906,203 A | 3/1990 | Margrave et al. |
| 4,907,589 A | 3/1990 | Cosman |
| 4,930,521 A | 6/1990 | Metzger et al. |
| 4,943,290 A | 7/1990 | Rexroth et al. |
| 4,947,842 A | 8/1990 | Marchosky et al. |
| 4,949,147 A | 8/1990 | Bacuvier |
| 4,955,377 A | 9/1990 | Lennox et al. |
| 4,966,597 A | 10/1990 | Cosman |
| 4,969,890 A | 11/1990 | Sugita et al. |
| 4,976,711 A | 12/1990 | Parins et al. |
| 4,979,948 A | 12/1990 | Geddes et al. |
| 4,998,539 A | 3/1991 | Delsanti |
| 5,006,119 A | 4/1991 | Acker et al. |
| 5,010,895 A | 4/1991 | Maurer et al. |
| 5,011,474 A | 4/1991 | Brennan |
| 5,011,488 A | 4/1991 | Ginsburg |
| 5,019,075 A | 5/1991 | Spears et al. |
| 5,035,696 A | 7/1991 | Rydell |
| 5,045,056 A | 9/1991 | Behl |
| 5,046,512 A | 9/1991 | Murchie |
| 5,047,028 A | 9/1991 | Qian |
| 5,056,532 A | 10/1991 | Hull et al. |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,117,828 A | 6/1992 | Metzger et al. |
| 5,122,137 A | 6/1992 | Lennox |
| 5,125,928 A | 6/1992 | Parins et al. |
| 5,151,100 A | 9/1992 | Abele et al. |
| 5,156,151 A | 10/1992 | Imran |
| 5,163,938 A | 11/1992 | Kambara et al. |
| 5,171,299 A | 12/1992 | Heitzmann et al. |
| 5,190,541 A | 3/1993 | Abele et al. |
| 5,192,297 A | 3/1993 | Hull |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,236,413 A | 8/1993 | Feiring |
| 5,242,441 A | 9/1993 | Avitall |
| 5,254,126 A | 10/1993 | Filipi et al. |
| 5,255,679 A | 10/1993 | Imran |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,169 A | 1/1994 | Afromowitz et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,305,696 A | 4/1994 | Mendenhall |
| 5,309,910 A | 5/1994 | Edwards et al. |
| 5,313,943 A | 5/1994 | Houser et al. |
| 5,314,438 A | 5/1994 | Shturman |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,375,594 A | 12/1994 | Cueva |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,411,025 A | 5/1995 | Webster, Jr. |
| 5,411,509 A | 5/1995 | Hilal |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Imran et al. |
| 5,423,812 A | 6/1995 | Ellman et al. |
| 5,428,658 A | 6/1995 | Oettinger et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,454,809 A | 10/1995 | Janssen |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,462,545 A | 10/1995 | Wang et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,517,989 A | 5/1996 | Frisbie et al. |
| 5,520,684 A | 5/1996 | Imran |
| 5,522,815 A | 6/1996 | Durgin, Jr. et al. |
| 5,524,622 A | 6/1996 | Wilson |
| 5,531,676 A | 7/1996 | Edwards et al. |
| 5,531,677 A | 7/1996 | Lundquist et al. |
| 5,533,958 A | 7/1996 | Wilk |
| 5,536,240 A | 7/1996 | Edwards et al. |
| 5,536,267 A | 7/1996 | Edwards et al. |
| 5,540,655 A | 7/1996 | Edwards et al. |
| 5,542,916 A | 8/1996 | Hirsch et al. |
| 5,542,928 A | 8/1996 | Evans |

(56) References Cited

U.S. PATENT DOCUMENTS

| | | |
|---|---|---|
| 5,549,644 A | 8/1996 | Lundquist et al. |
| 5,549,661 A | 8/1996 | Korkis et al. |
| RE35,330 E | 9/1996 | Malone et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,566,221 A | 10/1996 | Smith et al. |
| 5,569,241 A | 10/1996 | Edwards |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,591,195 A | 1/1997 | Taheri et al. |
| 5,599,345 A | 2/1997 | Edwards et al. |
| 5,609,151 A | 3/1997 | Mulier et al. |
| 5,621,780 A | 4/1997 | Smith et al. |
| 5,624,439 A | 4/1997 | Edwards et al. |
| 5,651,780 A | 7/1997 | Jackson et al. |
| 5,651,788 A | 7/1997 | Fleischer et al. |
| 5,658,278 A | 8/1997 | Imran et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,713,942 A | 2/1998 | Stern et al. |
| 5,716,410 A | 2/1998 | Wang et al. |
| 5,730,128 A | 3/1998 | Pomeranz et al. |
| 5,732,698 A | 3/1998 | Swanson et al. |
| 5,738,096 A | 4/1998 | Ben-Haim |
| 5,748,699 A | 5/1998 | Smith |
| 5,769,846 A | 6/1998 | Edwards et al. |
| 5,769,880 A | 6/1998 | Truckai et al. |
| 5,779,698 A | 7/1998 | Clayman et al. |
| 5,797,835 A | 8/1998 | Green |
| 5,797,903 A | 8/1998 | Swanson et al. |
| 5,800,334 A | 9/1998 | Wilk |
| 5,800,429 A | 9/1998 | Edwards |
| 5,820,629 A | 10/1998 | Cox |
| 5,823,197 A | 10/1998 | Edwards |
| 5,823,955 A | 10/1998 | Kuck et al. |
| 5,827,273 A | 10/1998 | Edwards |
| 5,827,304 A | 10/1998 | Hart |
| 5,830,213 A | 11/1998 | Panescu et al. |
| 5,833,688 A | 11/1998 | Sieben et al. |
| 5,836,874 A | 11/1998 | Swanson et al. |
| 5,842,984 A | 12/1998 | Avitall |
| 5,843,017 A | 12/1998 | Yoon |
| 5,846,196 A | 12/1998 | Siekmeyer et al. |
| 5,860,974 A | 1/1999 | Abele |
| 5,861,036 A | 1/1999 | Godin |
| 5,863,291 A | 1/1999 | Schaer |
| 5,871,483 A | 2/1999 | Jackson et al. |
| 5,876,340 A | 3/1999 | Tu et al. |
| 5,888,743 A | 3/1999 | Das |
| 5,891,134 A | 4/1999 | Goble et al. |
| 5,895,355 A | 4/1999 | Schaer |
| 5,902,263 A * | 5/1999 | Patterson et al. ............... 604/22 |
| 5,904,711 A | 5/1999 | Flom et al. |
| 5,925,044 A | 7/1999 | Hofmann et al. |
| 5,938,694 A | 8/1999 | Jaraczewski et al. |
| 5,964,755 A | 10/1999 | Edwards |
| 5,976,129 A | 11/1999 | Desai |
| 5,984,861 A | 11/1999 | Crowley |
| 5,997,534 A | 12/1999 | Tu et al. |
| 6,006,755 A | 12/1999 | Edwards |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson |
| 6,027,499 A | 2/2000 | Johnston et al. |
| 6,033,397 A | 3/2000 | Laufer et al. |
| 6,039,701 A | 3/2000 | Sliwa et al. |
| 6,041,260 A | 3/2000 | Stern et al. |
| 6,044,846 A | 4/2000 | Edwards |
| 6,053,172 A | 4/2000 | Hovda et al. |
| 6,053,913 A | 4/2000 | Tu et al. |
| 6,056,744 A | 5/2000 | Edwards |
| 6,059,719 A | 5/2000 | Yamamoto et al. |
| 6,068,629 A | 5/2000 | Haissaguerre et al. |
| 6,071,277 A | 6/2000 | Farley et al. |
| 6,073,052 A | 6/2000 | Zelickson et al. |
| 6,086,558 A | 7/2000 | Bower et al. |
| 6,091,993 A | 7/2000 | Bouchier et al. |
| 6,091,995 A | 7/2000 | Ingle et al. |
| 6,092,528 A | 7/2000 | Edwards |
| 6,095,966 A | 8/2000 | Chornenky et al. |
| 6,096,054 A | 8/2000 | Wyzgala et al. |
| 6,102,908 A | 8/2000 | Tu et al. |
| 6,112,123 A | 8/2000 | Kelleher et al. |
| 6,120,434 A | 9/2000 | Kimura et al. |
| 6,123,703 A | 9/2000 | Tu et al. |
| 6,123,718 A | 9/2000 | Tu et al. |
| 6,138,046 A | 10/2000 | Dalton |
| 6,142,994 A | 11/2000 | Swanson et al. |
| 6,146,149 A | 11/2000 | Daoud |
| 6,149,647 A | 11/2000 | Tu et al. |
| 6,162,237 A | 12/2000 | Chan |
| 6,179,836 B1 | 1/2001 | Eggers et al. |
| 6,182,666 B1 | 2/2001 | Dobak, III |
| 6,183,468 B1 | 2/2001 | Swanson et al. |
| 6,197,022 B1 | 3/2001 | Baker |
| 6,237,355 B1 | 5/2001 | Li |
| 6,238,392 B1 | 5/2001 | Long |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,258,118 B1 | 7/2001 | Baum et al. |
| 6,273,886 B1 | 8/2001 | Edwards et al. |
| 6,321,121 B1 | 11/2001 | Zelickson et al. |
| 6,325,798 B1 | 12/2001 | Edwards et al. |
| 6,325,800 B1 | 12/2001 | Durgin et al. |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,363,937 B1 | 4/2002 | Hovda et al. |
| 6,383,181 B1 | 5/2002 | Johnston et al. |
| 6,394,949 B1 | 5/2002 | Crowley et al. |
| 6,402,744 B2 | 6/2002 | Edwards et al. |
| 6,405,732 B1 | 6/2002 | Edwards et al. |
| 6,409,723 B1 | 6/2002 | Edwards |
| H0002037 H | 7/2002 | Yates et al. |
| 6,415,016 B1 | 7/2002 | Chornenky et al. |
| 6,416,511 B1 | 7/2002 | Lesh et al. |
| 6,423,058 B1 | 7/2002 | Edwards et al. |
| 6,425,877 B1 | 7/2002 | Edwards |
| 6,428,536 B2 | 8/2002 | Panescu et al. |
| 6,432,104 B1 | 8/2002 | Eurgin et al. |
| 6,440,128 B1 | 8/2002 | Edwards et al. |
| 6,448,658 B2 | 9/2002 | Takata et al. |
| 6,451,014 B1 | 9/2002 | Wakikaido et al. |
| 6,454,790 B1 | 9/2002 | Neuberger et al. |
| 6,464,697 B1 | 10/2002 | Edwards et al. |
| 6,468,272 B1 | 10/2002 | Koblish et al. |
| 6,514,246 B1 | 2/2003 | Swanson et al. |
| 6,514,249 B1 | 2/2003 | Maguire et al. |
| 6,535,768 B1 | 3/2003 | Baker et al. |
| 6,544,226 B1 | 4/2003 | Gaiser et al. |
| 6,547,776 B1 | 4/2003 | Gaiser et al. |
| 6,547,787 B1 | 4/2003 | Altman et al. |
| 6,551,302 B1 | 4/2003 | Rosinko et al. |
| 6,551,310 B1 | 4/2003 | Ganz et al. |
| 6,551,315 B2 | 4/2003 | Kortenbach et al. |
| 6,562,034 B2 | 5/2003 | Edwards et al. |
| 6,572,578 B1 | 6/2003 | Blanchard |
| 6,572,610 B2 | 6/2003 | Kovalcheck et al. |
| 6,572,639 B1 | 6/2003 | Ingle et al. |
| 6,575,966 B2 | 6/2003 | Lane et al. |
| 6,589,238 B2 | 7/2003 | Edwards et al. |
| 6,613,047 B2 | 9/2003 | Edwards |

(56) References Cited

U.S. PATENT DOCUMENTS

| | | | |
|---|---|---|---|
| 6,641,581 B2 | 11/2003 | Muzzammel | |
| 6,663,626 B2 | 12/2003 | Truckai et al. | |
| 6,673,070 B2 | 1/2004 | Edwards et al. | |
| 6,682,528 B2 | 1/2004 | Frazier et al. | |
| 6,689,130 B2 | 2/2004 | Arail et al. | |
| 6,695,764 B2 | 2/2004 | Silverman et al. | |
| 6,712,074 B2 | 3/2004 | Edwards et al. | |
| 6,712,814 B2 | 3/2004 | Edwards et al. | |
| 6,712,815 B2 | 3/2004 | Sampson et al. | |
| 6,740,082 B2 | 5/2004 | Shadduck | |
| 6,749,607 B2 | 6/2004 | Edwards et al. | |
| 6,752,806 B2 | 6/2004 | Durgin et al. | |
| 6,800,083 B2 | 10/2004 | Hiblar et al. | |
| 6,837,886 B2 | 1/2005 | Collins et al. | |
| 6,846,312 B2 | 1/2005 | Edwards et al. | |
| 6,860,878 B2 | 3/2005 | Brock | |
| 6,866,663 B2 | 3/2005 | Edwards et al. | |
| 6,872,206 B2 | 3/2005 | Edwards et al. | |
| 6,917,834 B2 | 7/2005 | Koblish et al. | |
| 6,918,906 B2 | 7/2005 | Long | |
| 6,923,808 B2 | 8/2005 | Taimisto | |
| 6,929,642 B2 | 8/2005 | Xiao et al. | |
| 6,953,469 B2 | 10/2005 | Ryan | |
| 6,964,661 B2 | 11/2005 | Rioux et al. | |
| 6,971,395 B2 | 12/2005 | Edwards et al. | |
| 6,974,456 B2 | 12/2005 | Edwards et al. | |
| 6,994,704 B2 | 2/2006 | Qin et al. | |
| 7,004,938 B2 | 2/2006 | Ormsby et al. | |
| 7,048,734 B1 | 5/2006 | Fleischman et al. | |
| 7,056,320 B2 | 6/2006 | Utley et al. | |
| 7,083,620 B2 | 8/2006 | Jahns et al. | |
| 7,089,063 B2 | 8/2006 | Lesh et al. | |
| 7,122,031 B2 | 10/2006 | Edwards et al. | |
| 7,125,407 B2 | 10/2006 | Edwards et al. | |
| 7,160,294 B2 | 1/2007 | Croft | |
| 7,165,551 B2 | 1/2007 | Edwards | |
| 7,167,758 B2 | 1/2007 | Baker et al. | |
| 7,179,257 B2 | 2/2007 | West et al. | |
| 7,293,563 B2 | 11/2007 | Utley et al. | |
| 7,326,207 B2 | 2/2008 | Edwards | |
| 7,329,254 B2 | 2/2008 | West et al. | |
| 7,416,549 B2 | 8/2008 | Young et al. | |
| 7,425,212 B1 | 9/2008 | Danek et al. | |
| 7,507,239 B2 | 3/2009 | Shadduck | |
| 7,680,543 B2 | 3/2010 | Azure | |
| 7,850,685 B2 | 12/2010 | Kunis et al. | |
| 8,012,149 B2 | 9/2011 | Jackson et al. | |
| 8,377,055 B2 | 2/2013 | Jackson et al. | |
| 8,398,631 B2 | 3/2013 | Ganz et al. | |
| 2001/0041887 A1 | 11/2001 | Crowley | |
| 2001/0051802 A1 | 12/2001 | Woloszko et al. | |
| 2002/0087151 A1 | 7/2002 | Mody et al. | |
| 2002/0147458 A1* | 10/2002 | Hiblar et al. | 606/159 |
| 2002/0177847 A1 | 11/2002 | Long | |
| 2002/0183739 A1* | 12/2002 | Long | 606/41 |
| 2003/0055452 A1 | 3/2003 | Joergensen et al. | |
| 2003/0069572 A1 | 4/2003 | Wellman et al. | |
| 2003/0093117 A1 | 5/2003 | Saadat | |
| 2003/0109837 A1 | 6/2003 | McBride-Sakal | |
| 2003/0153905 A1 | 8/2003 | Edwards et al. | |
| 2003/0158550 A1 | 8/2003 | Ganz et al. | |
| 2003/0181900 A1 | 9/2003 | Long | |
| 2003/0181905 A1 | 9/2003 | Long | |
| 2003/0191512 A1 | 10/2003 | Laufer et al. | |
| 2003/0216727 A1 | 11/2003 | Long | |
| 2004/0087936 A1 | 5/2004 | Stern et al. | |
| 2004/0122452 A1 | 6/2004 | Deem et al. | |
| 2004/0147916 A1 | 7/2004 | Baker | |
| 2004/0153120 A1 | 8/2004 | Seifert | |
| 2004/0172016 A1 | 9/2004 | Bek et al. | |
| 2004/0204708 A1 | 10/2004 | Edwards et al. | |
| 2004/0215180 A1 | 10/2004 | Starkebaum et al. | |
| 2004/0215235 A1 | 10/2004 | Jackson et al. | |
| 2004/0215296 A1 | 10/2004 | Ganz et al. | |
| 2004/0236316 A1 | 11/2004 | Danitz et al. | |
| 2004/0243124 A1 | 12/2004 | Im et al. | |
| 2005/0010162 A1 | 1/2005 | Utley et al. | |
| 2005/0033271 A1 | 2/2005 | Qin et al. | |
| 2005/0035096 A1* | 2/2005 | Kilburn | 219/121.68 |
| 2005/0070978 A1 | 3/2005 | Bek et al. | |
| 2005/0090817 A1 | 4/2005 | Phan | |
| 2005/0096713 A1 | 5/2005 | Starkebaum et al. | |
| 2005/0107829 A1 | 5/2005 | Edwards et al. | |
| 2005/0143727 A1 | 6/2005 | Koblish et al. | |
| 2005/0149013 A1 | 7/2005 | Lee | |
| 2005/0154386 A1 | 7/2005 | West et al. | |
| 2005/0159743 A1 | 7/2005 | Edwards et al. | |
| 2005/0171524 A1* | 8/2005 | Stern et al. | 606/41 |
| 2005/0187546 A1 | 8/2005 | Bek et al. | |
| 2005/0215983 A1 | 9/2005 | Brock | |
| 2005/0224474 A1* | 10/2005 | Kilburn | 219/121.68 |
| 2005/0245926 A1 | 11/2005 | Edwards et al. | |
| 2005/0288664 A1 | 12/2005 | Ford et al. | |
| 2006/0009758 A1 | 1/2006 | Edwards et al. | |
| 2006/0015162 A1 | 1/2006 | Edward et al. | |
| 2006/0020276 A1* | 1/2006 | Saadat et al. | 606/153 |
| 2006/0041256 A1 | 2/2006 | Edwards et al. | |
| 2006/0069303 A1 | 3/2006 | Couvillon | |
| 2006/0086363 A1 | 4/2006 | Qin et al. | |
| 2006/0095032 A1 | 5/2006 | Jackson et al. | |
| 2006/0259028 A1 | 11/2006 | Utley et al. | |
| 2006/0259029 A1 | 11/2006 | Utley et al. | |
| 2006/0259030 A1 | 11/2006 | Utley et al. | |
| 2006/0282071 A1 | 12/2006 | Utley et al. | |
| 2007/0066973 A1 | 3/2007 | Stern et al. | |
| 2007/0100333 A1 | 5/2007 | Jackson et al. | |
| 2007/0118104 A1 | 5/2007 | Wallace et al. | |
| 2007/0118106 A1 | 5/2007 | Utley et al. | |
| 2007/0118159 A1 | 5/2007 | Deem et al. | |
| 2007/0135809 A1 | 6/2007 | Utley et al. | |
| 2007/0167963 A1 | 7/2007 | Deem et al. | |
| 2007/0219570 A1 | 9/2007 | Deem et al. | |
| 2007/0255296 A1 | 11/2007 | Sauer | |
| 2007/0287994 A1 | 12/2007 | Patel | |
| 2007/0288001 A1 | 12/2007 | Patel | |
| 2008/0097427 A1 | 4/2008 | Stern et al. | |
| 2008/0275445 A1 | 11/2008 | Kelly et al. | |
| 2008/0319350 A1 | 12/2008 | Wallace et al. | |
| 2009/0012512 A1 | 1/2009 | Utley et al. | |
| 2009/0012513 A1 | 1/2009 | Utley et al. | |
| 2009/0012518 A1 | 1/2009 | Utley et al. | |
| 2009/0036886 A1 | 2/2009 | Utley et al. | |
| 2009/0177194 A1 | 7/2009 | Wallace | |
| 2009/0187181 A1 | 7/2009 | Shadduck | |
| 2009/0318914 A1 | 12/2009 | Utley | |
| 2010/0063495 A1 | 3/2010 | Utley et al. | |
| 2010/0191237 A1 | 7/2010 | Shadduck | |
| 2011/0270249 A1 | 11/2011 | Utley et al. | |
| 2012/0004656 A1 | 1/2012 | Jackson | |
| 2012/0239028 A1 | 9/2012 | Wallace et al. | |

FOREIGN PATENT DOCUMENTS

| | | |
|---|---|---|
| EP | 0105677 | 4/1984 |
| EP | 0115420 | 8/1984 |
| EP | 0139607 | 5/1985 |
| EP | 0251745 | 1/1988 |
| EP | 0521595 A2 | 1/1993 |
| EP | 0608609 | 8/1994 |
| EP | 1323382 A1 | 7/2003 |
| EP | 1634542 B1 | 3/2006 |
| JP | H07171156 | 7/1995 |
| JP | 8506738 | 7/1996 |
| JP | 2003510160 A | 3/2003 |
| JP | 2005503181 | 2/2005 |
| WO | 9101773 | 2/1991 |
| WO | 9103207 A1 | 3/1991 |
| WO | 9210142 | 6/1992 |
| WO | 9308755 | 5/1993 |
| WO | 9407446 A1 | 4/1994 |
| WO | 9410925 | 5/1994 |

(56) References Cited

FOREIGN PATENT DOCUMENTS

| WO | 9421165 | 9/1994 |
| WO | 9421178 | 9/1994 |
| WO | 9422366 | 10/1994 |
| WO | 9426178 | 11/1994 |
| WO | 9518575 | 7/1995 |
| WO | 9519142 | 7/1995 |
| WO | 9525472 | 9/1995 |
| WO | 9600042 | 1/1996 |
| WO | 9616606 | 6/1996 |
| WO | 9629946 | 10/1996 |
| WO | 9704702 | 2/1997 |
| WO | 9706857 | 2/1997 |
| WO | 9732532 | 9/1997 |
| WO | 9743971 | 11/1997 |
| WO | 9812999 A2 | 4/1998 |
| WO | 9814238 A1 | 4/1998 |
| WO | 9818393 A1 | 5/1998 |
| WO | 9903413 | 1/1999 |
| WO | 9935987 | 7/1999 |
| WO | 9942046 | 8/1999 |
| WO | 9955245 | 11/1999 |
| WO | 0001313 | 1/2000 |
| WO | 0059393 | 10/2000 |
| WO | 0062699 A2 | 10/2000 |
| WO | 0066017 A1 | 11/2000 |
| WO | 0066021 | 11/2000 |
| WO | 0066052 A1 | 11/2000 |
| WO | 0069376 A1 | 11/2000 |
| WO | 0122897 A1 | 4/2001 |
| WO | 0135846 | 5/2001 |
| WO | 0145550 A2 | 6/2001 |
| WO | 0189440 | 11/2001 |
| WO | 02096327 A2 | 12/2002 |
| WO | 03070091 A1 | 8/2003 |
| WO | 2004043280 A1 | 5/2004 |
| WO | 2006116019 A2 | 11/2006 |
| WO | 2007001981 A2 | 1/2007 |
| WO | 2007061984 A2 | 5/2007 |

OTHER PUBLICATIONS

Dallamagne et al.; Laparoscopic Nissen Fundoplication: Preliminary. Surgical Laparoscopy and Endoscopy. 1991; 1(3):138-143.
Hinder et al.; the Technique of Laparoscopic Nissen Fundoplication. Surgical Laparoscopy and Endoscopy. 1992; 2(3):265-272.
Kaneko et al.; Physiological Laryngeal Pacemaker. Trans Am. Soc. artif Intern Organs. 1985; XXXI:293-296.
Karlstrom et al.; Ectopic Jejunal Pacemakers and Enterogastric Reflux Roux gastrectomy: Effect of Intestinal Pacing. Surgery. 1989; 106(3):486-495.
Kelly, K. A. et al.; Duodenal-Gastric Reflux and Slowed Gastric Emptying by Electrical pacing of the Canine Duodenal Pacesetter Potential. Gastroenterology. 1977; 72(3):429-433.
Mugica, et al. Direct Diaphragm Stimulation. PACE. 1987; 10:252-256.
Mugica, et al., Preliminary Test of a Muscular Diaphragm Pacing System on Human Patients. Neurostimulation: an Overview, chapter 21. 1985; 263-279.
Reynolds, J.C., Influence of Pathophysiology, Severity, and Cost on the Medical Management of Gastroesophageal Reflux Disease. Am J. Health-syst Phar. 1996; 53(22sul3): S5-S12.
Rice et al.; Endoscopic Paranasal Sinus Surgery. Chapter 5, Functional Endoscopic Paranasal Sinus Surgery, the Technique of Messerklinger. Raven Press. 1988; 75-102.
Rice et al.; Enoscopic Paranasal Sinus Surgery. Chapter 6, Total Endoscpic Sphenoethmoidectomy. The Technique of Wigand. Raven Press. 1988; 103-125.
Salameh et al.; An Animal Model Study to Clarify and Investigate Endoscopic tissue Coagulation by Using a New Monopolar Device. Gastrointestinal Endoscopy; 2004; 59(1): 107-112.
Urshel, J.D. Complications of Antireflux Surgery. Am J. Surg. 1993; 166(1):68-70.
DiabetesInControl.com, "How tummy surgery cures diabetes in a matter of days," (website accessed Jun. 6, 2007).
Drucker, The role of gut hormones in glucose homeostasis, The Journal of Clinical Investigation, vol. 117, No. 1, Jan. 2007.

* cited by examiner

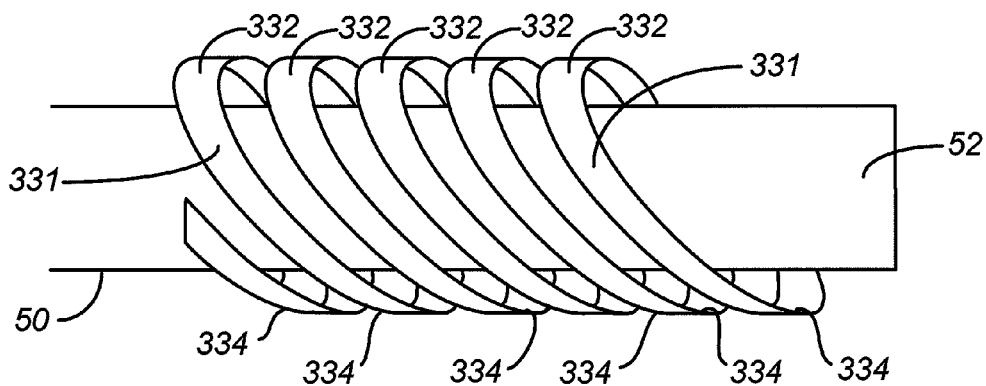
FIG. 17
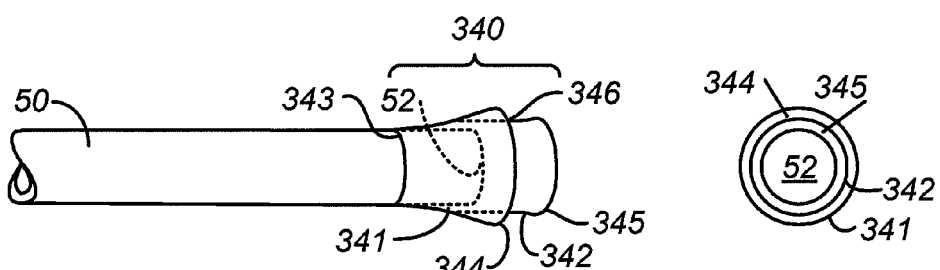
FIG. 18A  FIG. 18B
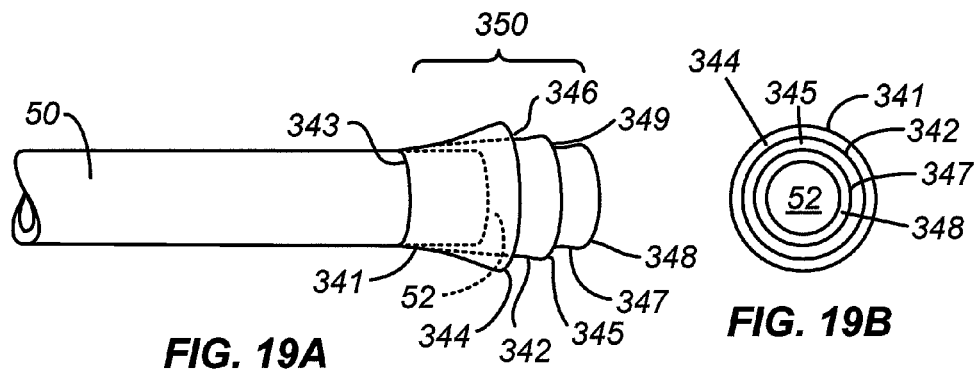
FIG. 19A  FIG. 19B

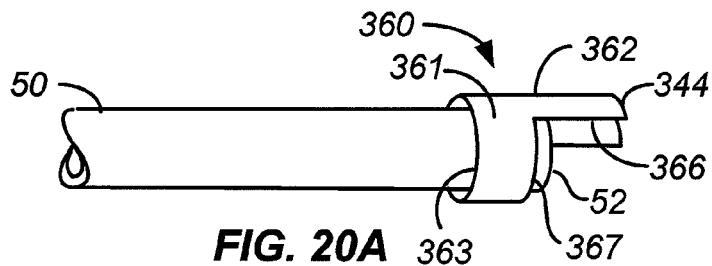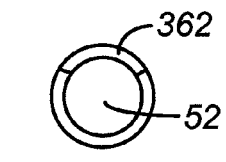
FIG. 20A        FIG. 20B
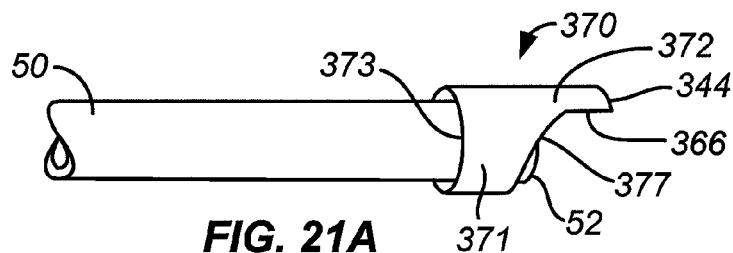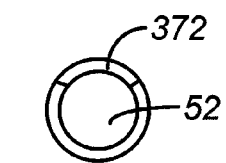
FIG. 21A        FIG. 21B
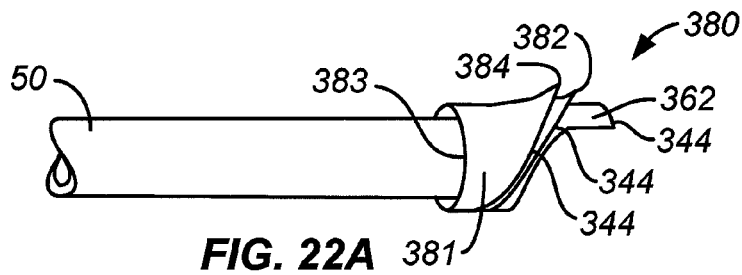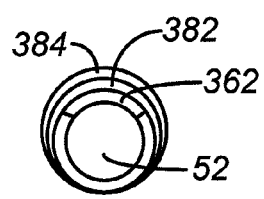
FIG. 22A        FIG. 22B
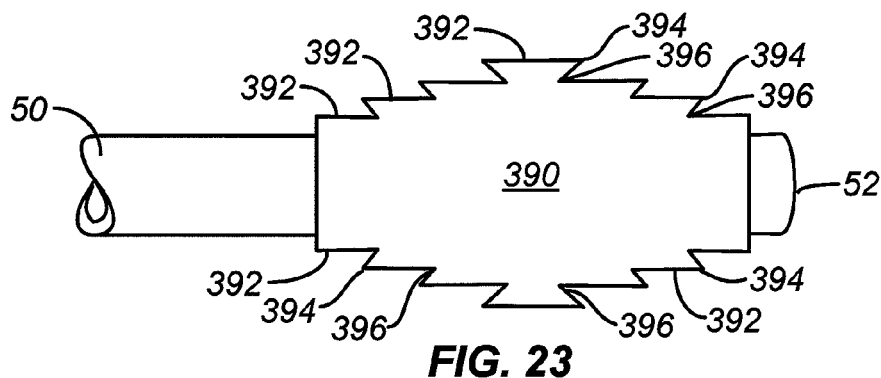
FIG. 23
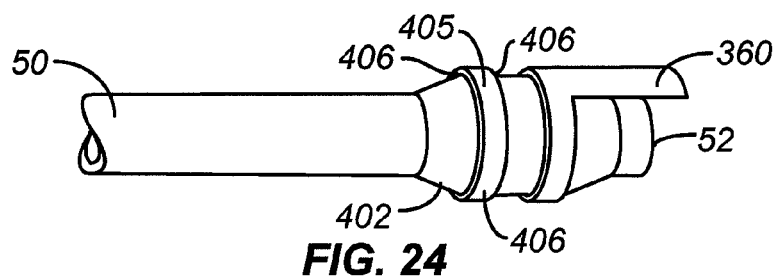
FIG. 24

CLEANING DEVICE AND METHODS

INCORPORATION BY REFERENCE

This application is a continuation of U.S. patent application Ser. No. 11/830,251, filed Jul. 30, 2007, by Wallace, et al., entitled "CLEANING DEVICE AND METHODS," which is incorporated herein by reference in its entirety for all purposes. All publications and patent applications mentioned in this specification are herein incorporated by reference to the same extent as if each individual publication or patent application was specifically and individually indicated to be incorporated by reference

FIELD OF THE INVENTION

Aspects of the invention relate to the removal of tissue between treatment procedures. In one application, embodiments of the present invention provide cleaning devices and methods useful in removing debris from tissue treatments. In other applications, embodiments of the invention provide cleaning devices and methods useful in preparing the tissue or area of a treatment site in advance of treatment by removing mucus, blood and alimentary tract by products such as bile and feces, for example.

BACKGROUND OF THE INVENTION

During ablation procedures to treat various disease states, previously treated tissue in the ablation field can impair subsequent ablation of the same area if the treated tissue remains adherent to the ablation zone. Effectiveness of subsequent ablation will be diminished if treated tissue is still present. To improve the procedure and efficacy of ablation, devices and techniques are needed to remove previously treated tissue prior to subsequent ablation.

SUMMARY OF THE INVENTION

In one aspect, embodiments of the present invention provide an apparatus for treating tissue within a lumen that include a therapeutic or diagnostic instrument and a cleaning device supported by the instrument having a proportion of a cleaning surface positioned proximal to the distal end of the cleaning device. In one embodiment, the cleaning device comprises a porous material or a porous material having open cells. In another aspect, a portion of the cleaning device comprises a blunt edge. In one aspect, the blunt edge is supported by one or more of a frame, a ridge or a ring.

In another aspect, the cleaning device is shaped to mount onto the instrument. Additionally, the cleaning device may also include an adhesive surface used to secure the cleaning device to the instrument. There may also be a sheath around at least portion of the cleaning device. In one embodiment, there is provided a chamber in the instrument for cleaning the cleaning device. In some embodiments, the therapeutic or diagnostic instrument is an endoscope. In one aspect, the cleaning device remains in a stowed condition during movement to a treatment site. In another aspect, the cleaning device is movable between a stowed condition adjacent the instrument and a deployed condition for engaging tissue on the lumen. In one aspect, the diameter of the cleaning device in the stowed condition is less than the diameter of the cleaning device in the deployed condition.

In still other embodiments, the cleaning device is formed from a compressible material. The cleaning device may also be formed from a compressible, porous material having at least one blunt edge on the exterior of the device. In one embodiment, there is a cavity in the cleaning device for storing a portion of the tissue from the lumen. In one specific aspect, the cavity is a pore of the cleaning device.

In one specific aspect, the cleaning device is a brush. In another specific aspect, the cleaning device is a balloon. Additionally, the balloon may also include a surface textured for tissue removal. In other additional aspects, the cleaning device is releasably joined to the exterior surface of the instrument. In furtherance of this aspect, the cleaning device is shaped to conform to the outer surface of a portion of the instrument.

In still other aspects, there is provided another cleaning surface on the cleaning device that is non-continuous with the cleaning surface. In one aspect, the cleaning device has a proximal end and a distal end and the proximal end has a circumference that nearly matches the circumference of the instrument and the distal end that has a circumference larger than the instrument. In another aspect, the cleaning surface is positioned on the distal end of the cleaning device and the another cleaning surface is on a tapered surface extending from the distal end of the cleaning device. In some embodiments, there is a recess between the cleaning surface and the another cleaning surface. In an additional aspect, the cleaning surface and the another cleaning surface are rings at least partially extending about the instrument. Additionally, at least one of the rings is helically arranged around the instrument. Alternatively, a compressible element is positioned between the instrument and the rings. The compressible element may include a porous material.

In another aspect, the cleaning surface or the another cleaning surface comprises an edge. In one embodiment, the edge is supported by one or more of a frame, a ridge or a ring. In another aspect, the cleaning device is shaped to mount onto the instrument. Additionally, there may be an elastic mounting component on the cleaning device adapted and configured to secure the cleaning device to the instrument. Additionally, there may be a sheath around at least a portion of the cleaning device that holds the cleaning surface or the another cleaning surface against the instrument. In one aspect, the cleaning device is moveable between a stowed condition where at least one cleaning surface is against the instrument and a deployed condition where at least one cleaning surface extends from the instrument.

In another aspect, at least one of the cleaning surface or the another cleaning surface is on the sidewall of the instrument. Additionally, a cleaning surface is positioned along the longitudinal axis of the cleaning device. Still further, a cleaning surface may be a ring at least partially extending about the instrument. The cleaning device may include a compressible element, a porous material and/or an edge.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

FIG. 17 is a perspective view of a cleaning device positioned to on the distal end of an instrument;

FIGS. 18A and 18B are perspective and end views, respectively, of a cleaning device positioned on the distal end of an instrument;

FIGS. 19A and 19B are perspective and end views, respectively, of a cleaning device positioned on the distal end of an instrument;

FIGS. 20A and 20B are perspective and end views, respectively of a cleaning device positioned on the distal end of an instrument;

FIGS. 21A and 21B are perspective and end views, respectively, of a cleaning device positioned on the distal end of an instrument;

FIGS. 22A and 22B are perspective and end views, respectively, of a cleaning device positioned on the distal end of an instrument;

FIG. 23 is a perspective view of a cleaning device positioned on the distal end of an instrument;

FIG. 24 is a perspective view of a cleaning device positioned on the distal end of an instrument;

DETAILED DESCRIPTION OF THE INVENTION

Figure 1:
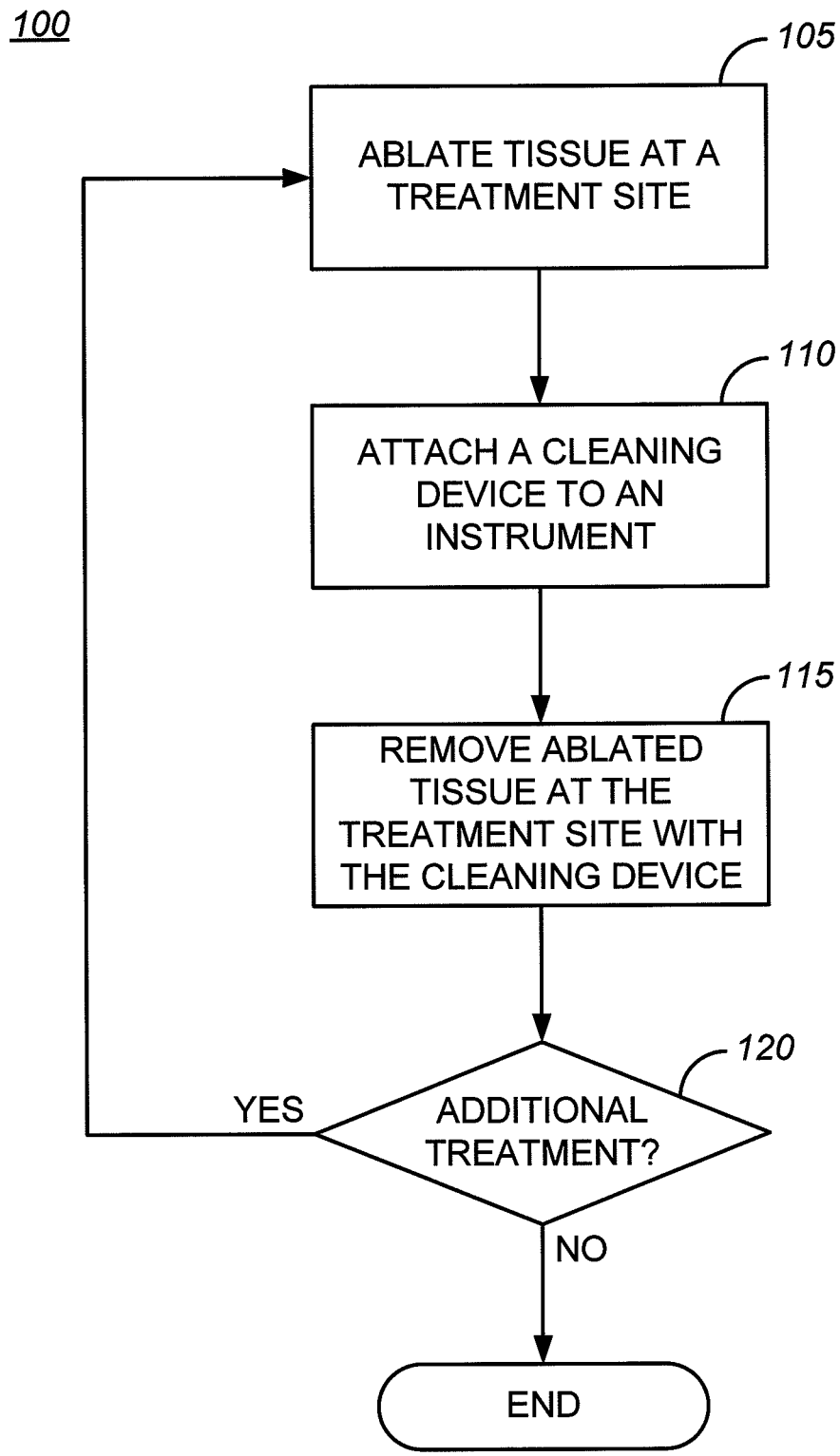
FIG. 1 is a flowchart illustrating one method of the invention.
Figure 3:
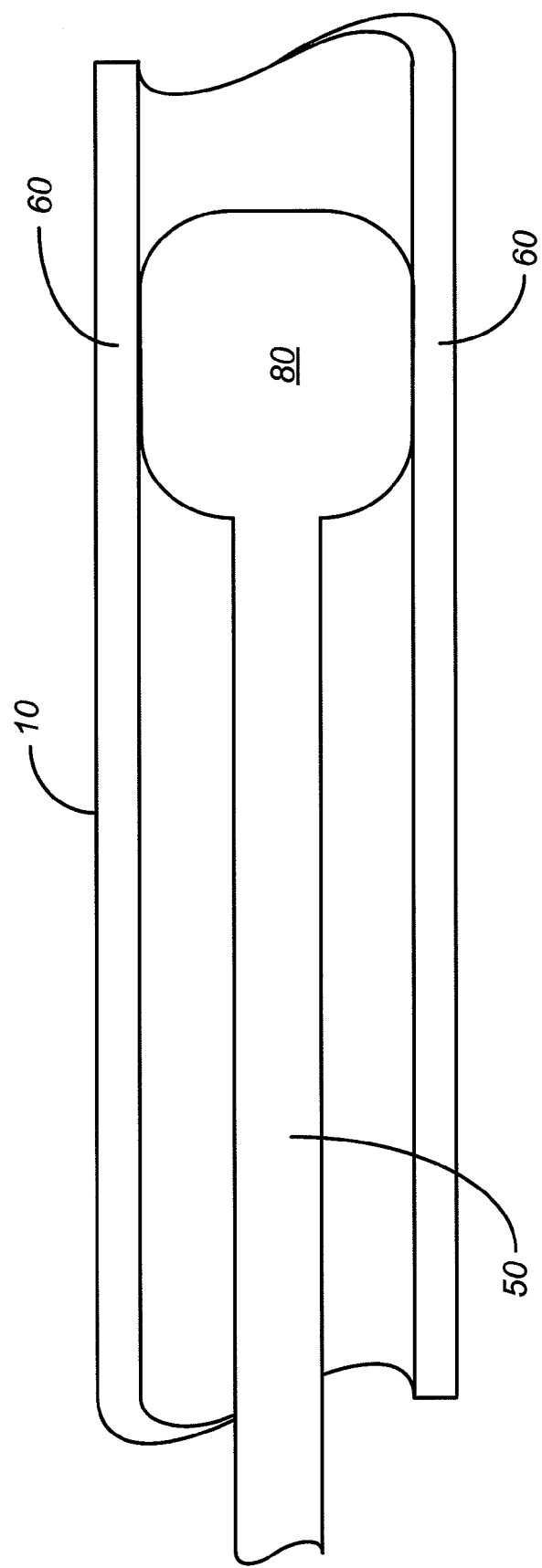
FIG. 3 illustrates the use of an ablation device within the esophagus.
Figure 4:
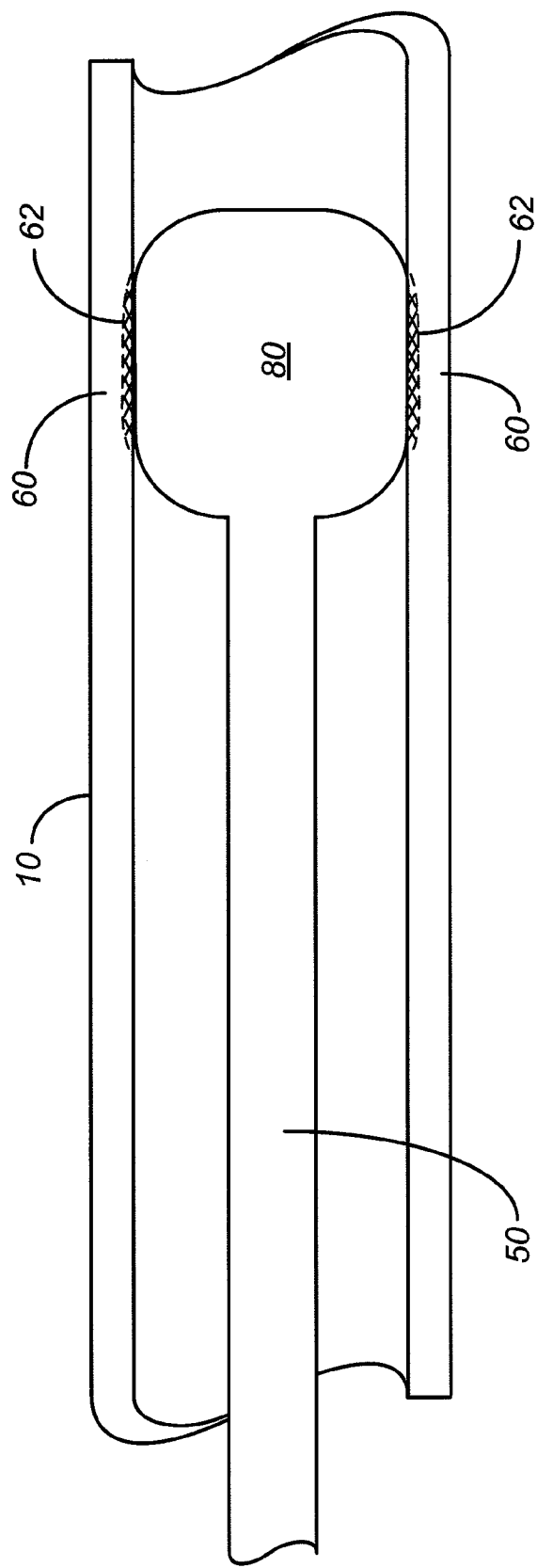
FIG. 4 illustrates treatment sites created within the esophagus as a result of ablation.

FIG. 1 is a flow chart 100 illustrating one embodiment of method of the invention. First, at step 105, ablate tissue at a treatment site. FIG. 3 illustrates the placement of an ablation device 80 within the esophagus 10 at a treatment site 60. The ablation device 80 may be any device configured to ablate targeted tissue using any suitable ablation technique. Ablation may be achieved through any known technique and using any of the wide variety of energy forms including the non-limiting examples of radiofrequency (RF, IR light, laser cryogenic, steam, convective heat, microwave and ultrasound. FIG. 4 illustrates a treatment site 60 or sites created within the esophagus 10 as a result of ablation the ablation procedures. After ablation, treated tissue 62 is present at the treatment site 60.

Returning to FIG. 1, next at step 110, attach a cleaning device to an instrument. Numerous alternative cleaning device designs are described below. Alternatively the cleaning device may be attached to the instrument before the ablation occurs and/or be present while ablation occurs. The instrument may be a shaft of sufficient length to allow the cleaning device to reach a treatment site within the body. The instrument may also be an endoscope or other therapeutic or diagnostic instrument. As used herein, a cleaning device is any device adapted for removing tissue from the treatment site using abrasion, scraping, rubbing, alone or in any combination. A cleaning device may be attached to an instrument permanently, formed as part of a unitary structure or may be removable from the instrument. A cleaning device may be a single use or reusable, with or without sterilization.

Figure 2:
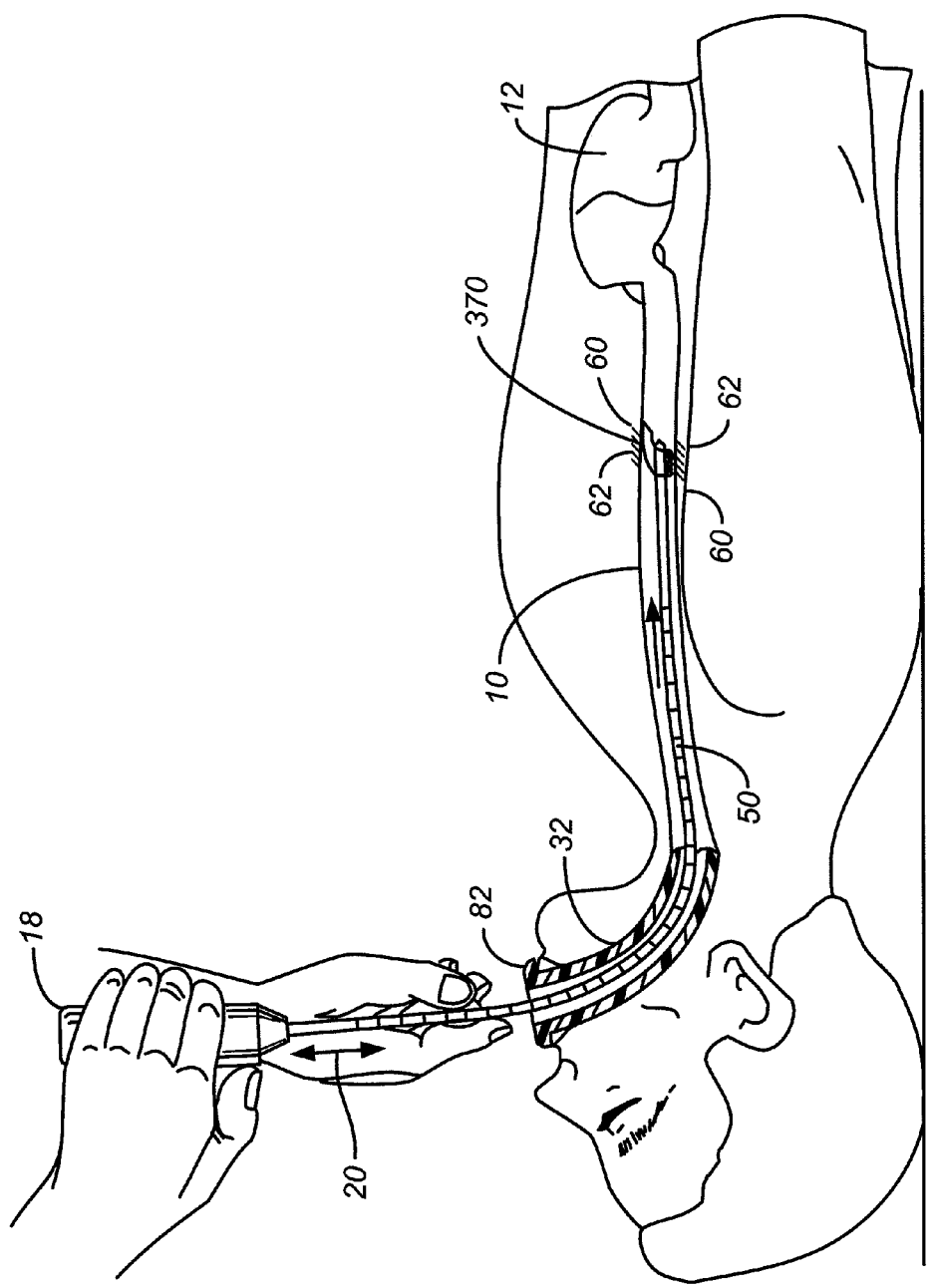
FIG. 2 illustrates the use of a cleaning device within the esophagus.

FIG. 2 illustrates the placement and use of a cleaning device 370 within the esophagus 10 at a treatment site 60. First, the cleaning device 370 is attached to the distal end of the instrument 50. The instrument 50 is advanced through the mouth (an insertion tube 82 is shown in place in the mouth), past the pharynx 32 and into the esophagus 10.

In some embodiments, while the cleaning device passes any narrowed areas, such as the pharynx or upper esophageal sphincter, the device moves to a smaller size configuration against the instrument. After passing the constriction, the cleaning device expands back to its fully deployed size. In this way, the device is in a deployed condition when the device is finally positioned at the treatment site. The characteristic of moving between a stowed and deployed condition could be a function of the compressible material in the cleaning device as in the embodiments of FIGS. 9A-14. Additionally or alternatively the characteristic of moving between a stowed and deployed condition could be a function of: the use of malleable scrapers as in FIGS. 18A-24; through the use of a sheath as in FIG. 25; or the use of a stowage chamber or working channel as an FIG. 26A.

Figure 5:
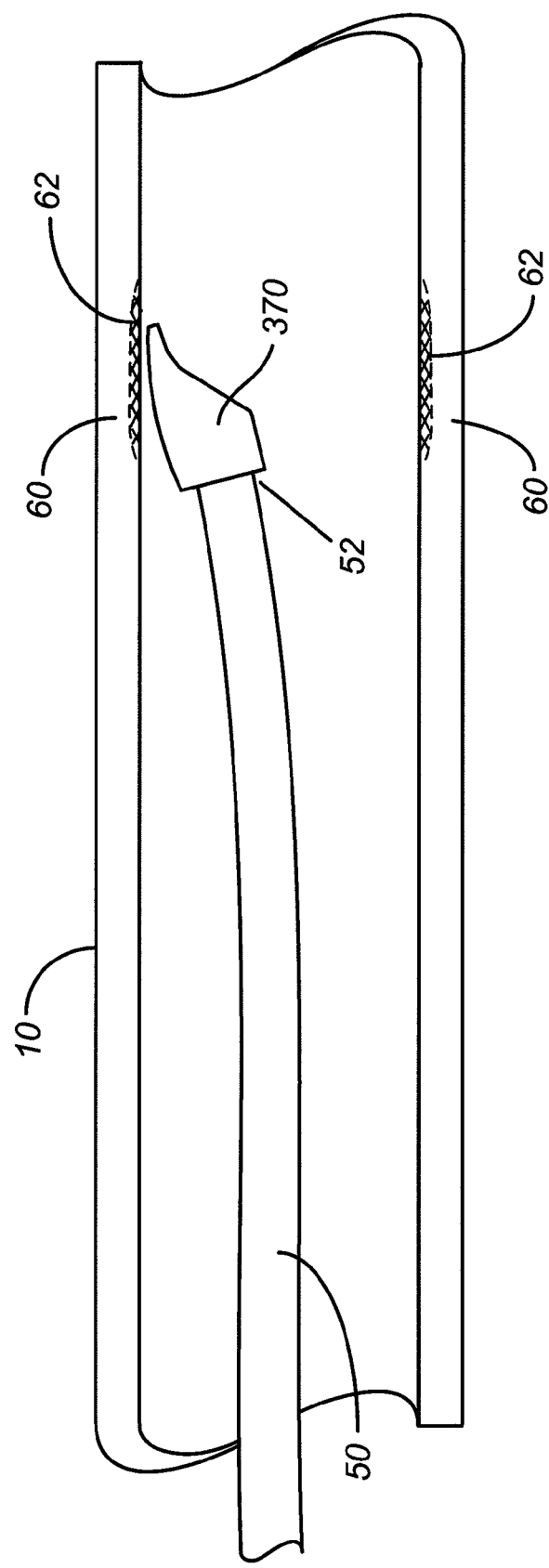
FIG. 5 illustrates a cleaning device positioned at a treatment site.

The instrument 50 is advanced along the esophagus 10 until the cleaning device 370 is positioned in the desired location within the treatment site 60. FIG. 5 illustrates a close-up view of cleaning device 370 in proximity to the treatment site 60. Visualization of the esophagus and the treatment site are provided by the instrument 50. Returning to FIG. 2, the cleaning device 370 is moved relative to the treatment site 60 by moving the instrument handle 18 as indicated by the arrows 20. Relative movement and contact between the cleaning device 370 and the treatment site 60 results in removal of treated tissue 62 from the treatment site 60 using any of a number of mechanisms alone or in any combination. Relative movement between the cleaning device 370 and the treatment site 60 may be produced by rotating, vibrating, oscillating, or other movement of the cleaning device 370 or a cleaning surface of a cleaning device in relation to the treated tissue 62 at the treatment site 60.

Figure 6:
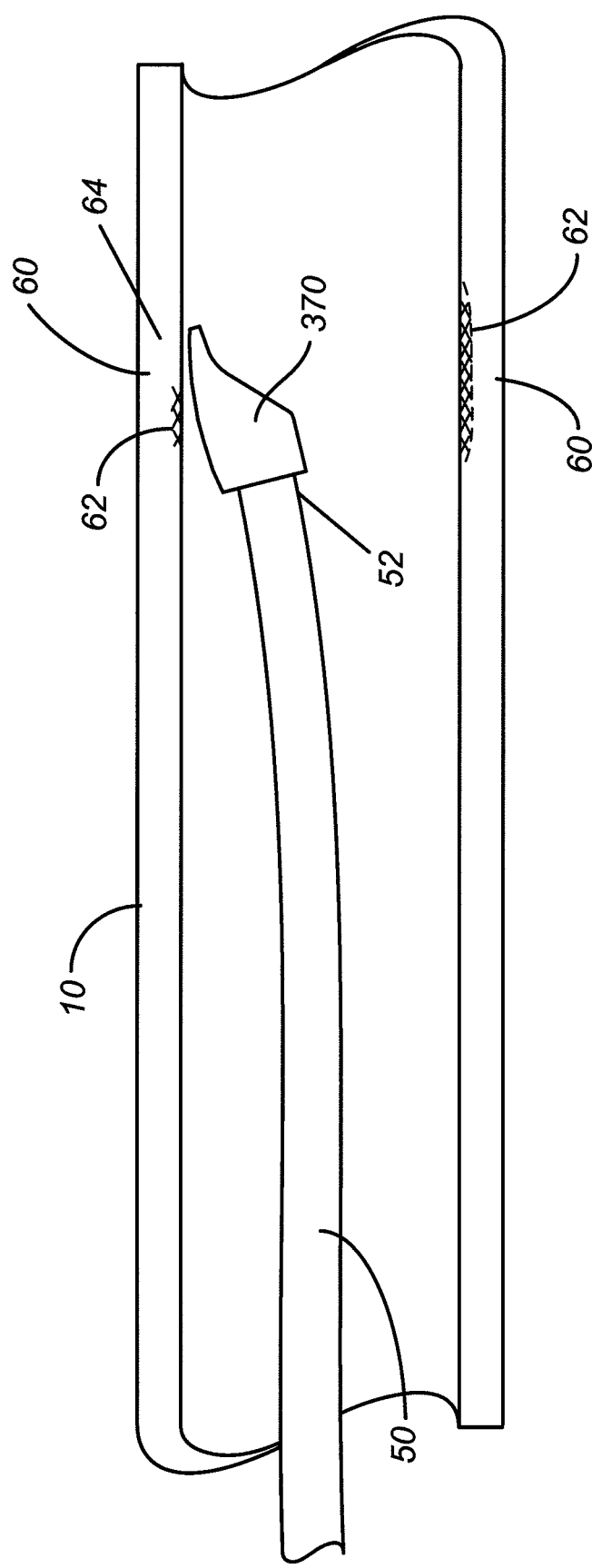
FIG. 6 illustrates the use of a cleaning device to remove treated tissue from a treatment site.

Returning to FIG. 1, next at step 115, remove ablated tissue at the treatment site with the cleaning device. FIG. 6 illustrates the use of a cleaning device 370 to remove treated tissue 62 from a treatment site 60. The initial use of the cleaning device 370 produced the cleaned site 64 where the ablated tissue 62 was removed. Ablated tissue 62 remains at the treatment site 60. The cleaning device 370 and cleaning process continues until the ablated tissue 62 is removed or until the treatment site 60 is adequately prepared for a follow on ablation step, if desired. Once cleaning is completed or sufficiently complete such that ablation may resume, the treatment site 60 returns to the condition illustrated in FIG. 3 where the treatment site 60 is ready for ablation and the ablation device 80 is in position.

Tissue removal may be accomplished through physical contact between a cleaning surface or portion of the cleaning device and the tissue at the treatment site. The cleaning device may be used in conjunction with flushing of the treatment site with liquids or air provided by the instrument. The cleaning device may be manipulated to remove tissue through any of a number of different mechanisms. Embodiments of the cleaning devices of the present invention may remove tissue from a treatment site through abrasion, scraping and/or rubbing. As will be appreciated in the description that follows, one or more cleaning surfaces of a cleaning device may be configured for rubbing, abrasion and/or scraping tissue.

Returning to FIG. 1, next at step 120, determine whether an additional treatment is needed at the treatment site. Based on the individual needs of the patient, multiple ablation steps may be performed in order to accomplish the desired amount of tissue removal. Alternatively, it may be desirable for multiple ablations between cleaning steps. If additional treatment is needed, return to step 105 and ablate tissue at a treatment site. If no additional treatment is needed, the method ends. Steps 105, 110 and 115 may, if desired, be repeated numerous times to provide a method of treatment where by ablated tissue from a previous ablation therapy is removed from a treatment site before a subsequent ablation therapy is provided at the treatment site. It is believed that the intermediate step of removing tissue from a previous ablation step increases the efficiency and efficacy of subsequent ablation steps. Also the uniformity of the tissue (no debris) enables a more controlled and safer ablation.

Figure 7A:
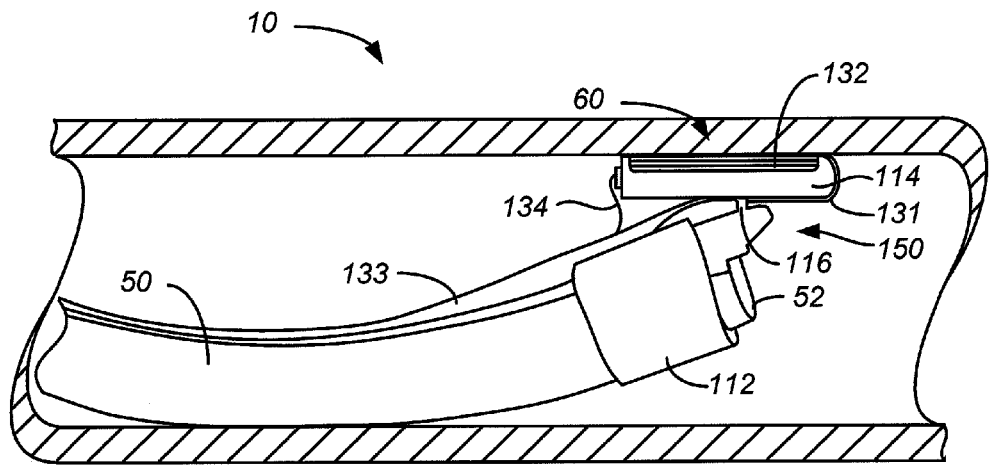
FIGS. 7A and 7B illustrate perspective and end views, respectively of an ablation device.
Figure 7B:
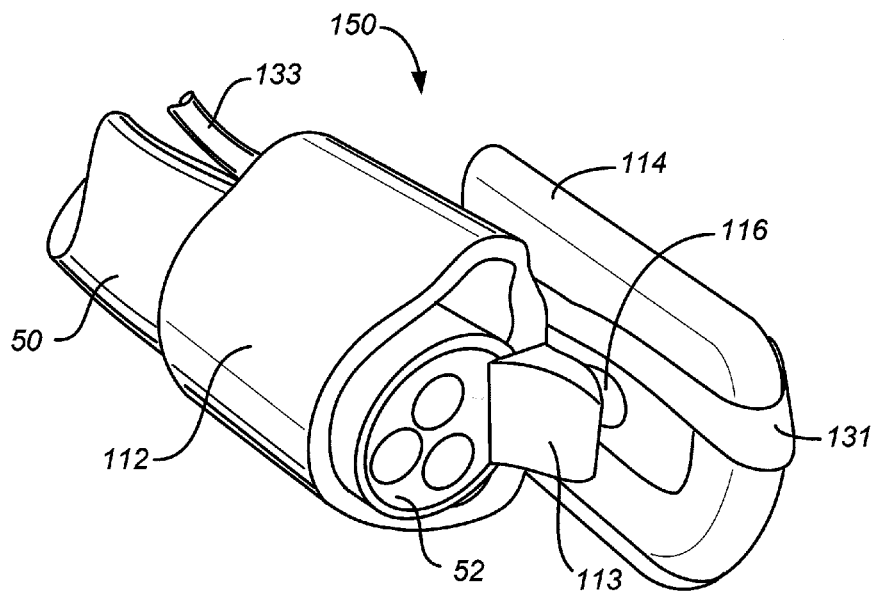

FIGS. 7A and 7B illustrate perspective and end views, respectively, of an ablation device 150 positioned on the distal end 52 of an instrument 50. The ablation device 150 includes suitable electrical connections including conductive wires 133 to connect the ablation structure 130 to a power source (not shown) as is conventional in the RF ablation arts. The conductive wires 133 can be wrapped or drawn over a distal end of the longitudinal support 114 and pass beneath the support 114. Such an arrangement advantageously facilitates rotational movement of the longitudinal support 114 by preventing binding or restriction of rotational movement. Additionally or alternately, the ablation device 150 can further include one or more electrode trace 131. The one or more electrode trace 131 can be constructed and arranged to conform to at least a portion of the longitudinal support 114. The one or more trace 131 can be in electrical communication with an electrode 132 and conductive wire 133.

FIG. 7A illustrates the ablation device 150 in position at a treatment site 60 within the esophagus 10 prepared for use in methods for ablating tissue. The ablation structure 132 is rotationally deflectable toward tissue at the target site 60 surface and the ablation structure 132 is activatable to ablate tissue at the target site 60. The ablation structure 132 is supported by an ablation device support structure. The ablation device support structure includes a base 112 with a longitudinal support 114 and a rotational support 116.

As best seen in FIG. 7B, the base 112 can be constructed and arranged in any of a number of ways to support the ablation device 150. In the illustrated embodiment, the base 112 is constructed and arranged to attach the ablation device 150 to an outside surface of the instrument 50, here an endoscope. The base 112 may also be constructed and arranged as a sheath and may also include a connecting element, a band or a strap to further secure the ablation device 150 to the instrument 50. In the illustrated embodiment, the base 112 includes a stop or lip 113 feature. The lip 113 can be constructed and arranged to function as a stop designed to aid in positioning the ablation device 150 in relation to the instrument 50.

The longitudinal support 114 is also constructed and arranged to support the ablation structure 132 in cooperation with the base 112. The support 114 can be made of any suitable material for withstanding the high energy flux produced by the ablation structure 130. The longitudinal support 114 can be flexible, enabling rotation about two axes, thereby further permitting rotation of the longitudinal support 114 away from the longitudinal axis (not shown). In one embodiment the longitudinal support is made of an elastic material, for example, silicone. Other suitable materials include, for example, urethanes or other polymers.

The rotational support 116 is adapted to permit at least a port of the ablation structure 132 to rotate with respect to the longitudinal support's longitudinal axis.

As best seen in FIG. 7A, an actuator mechanism 134 is provided for actively governing the rotation of the longitudinal support 114. Generally the actuator mechanism 134 permits interconversion between a rotationally constrained longitudinal support 114 and free rotation of the support 114. Additional details of the various aspects of the construction and operation of ablation devices are described in United States Patent Application Publication US 2007/0118104 titled "Auto-Aligning Ablating Device and Method of Use" commonly assigned to the assignee of the present application and incorporated herein by reference in its entirety.

Figure 8A:
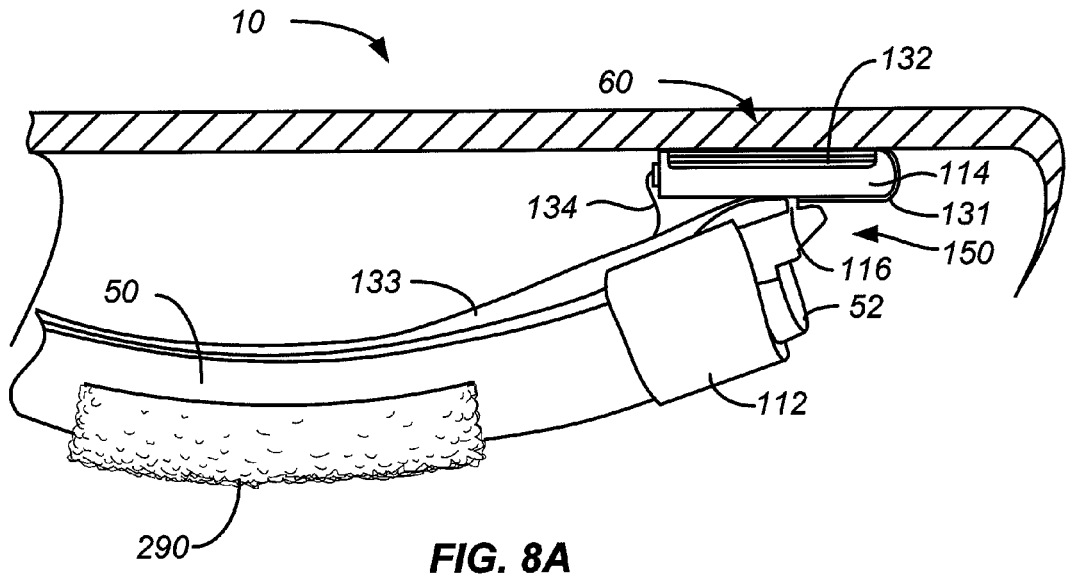
FIGS. 8A and 8B illustrate perspective and end views, respectively, of an ablation device with a cleaning device.
Figure 8B:
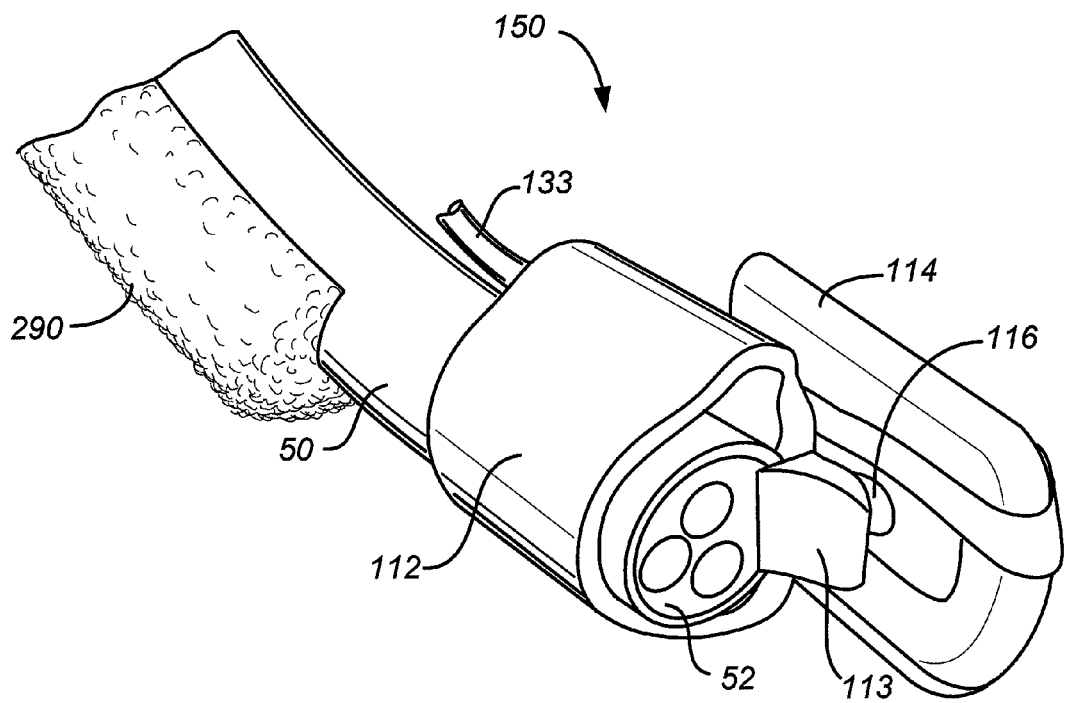

FIGS. 8A and 8B illustrate perspective and end views, respectively of the ablation device of FIGS. 7A and 7B with a cleaning device 290 attached. In the illustrated embodiment, the cleaning device 290 is an embodiment of the device illustrated in FIG. 14. The cleaning device 290 has a slot 293 sized to fit over the shaft of an instrument 50. The inner surface of the cleaning device may include an adhesive to affix the cleaning device to the instrument 50. The cleaning device slot 293 may be configured to secure the cleaning device 290 to the instrument 50 with a friction lock. As shown in FIGS. 8A and 8B, the slot 293 is sized to fit onto and secure the cleaning device 290 to the shaft of the instrument 50.

Figure 9A:
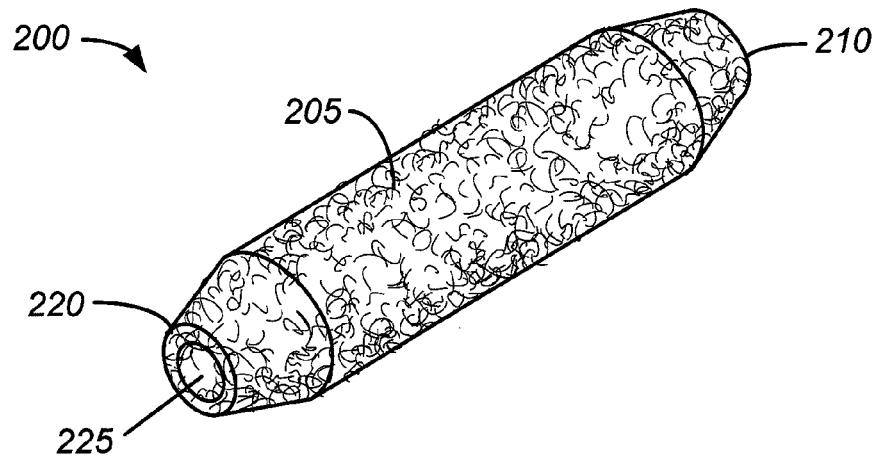
FIGS. 9A, 9B and 9C illustrate perspective, end and cross section views of a cleaning device.
Figure 9B:
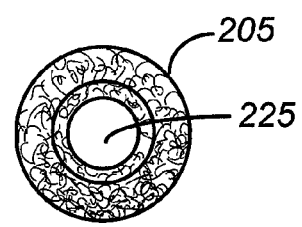
Figure 9C:
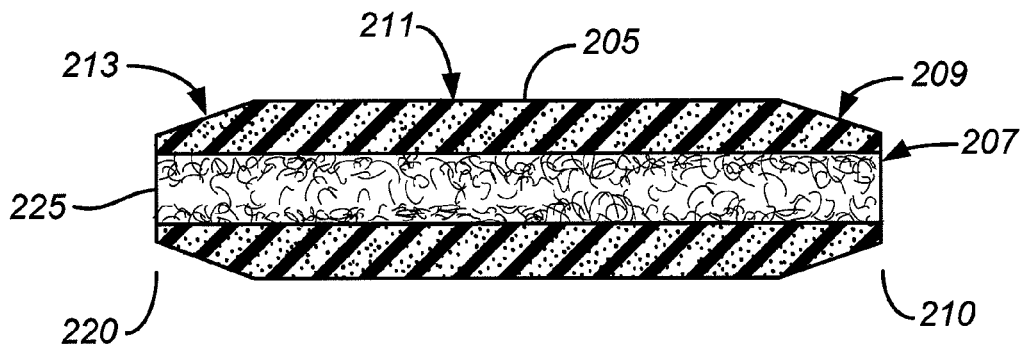

FIGS. 9A, 9B and 9C illustrate perspective, end and cross section views of a cleaning device 200. The cleaning device 200 includes a body 205 having a distal end 210 and a proximal end 220 and an opening 225 on the proximal end sized to fit onto the distal end 52 of an instrument 50. The cleaning device distal end 210 may be closed so that the cleaning device 200 remains on the distal end of the instrument. Alternatively, the cleaning device distal end 210 may be opened so that the cleaning device 200 may be advanced proximal to the distal end 52 of the instrument 50.

The cleaning devices described herein may be formed from any of a wide variety of abrasive materials including compressible and non-compressible materials. For example, the cleaning device 200 may be formed from porous or foam materials, including but not limited to: polyurethane esters, polyurethane ethers, micro-cellular urethanes, latex foams, natural sponge rubber, filter foams, conductive foams, melamine polyamide, polyesters, polyethers, polyethylene, chemically cross-linked polyethylene, irradiation cross-linked polyethylene, EVA, neoprene, EPDM, nitrile vinyl, PVC, nylon, silicone, PTFE, EPTFE, open or closed cell forms, reticulated or non-reticulated foam structures, and plasma treated structures to increase material hydrophobicity.

Cleaning devices of the present invention may include one or more cleaning surfaces. The multiple cleaning surfaces provided by the cleaning device 200 are best seen in FIG. 9C. The distal end 210 may include an edge or shaped surface 207. The angled surface proximal to the distal end may provide an additional cleaning surface 209. Another cleaning surface 211 may be provided along the longitudinal axis of the cleaning device body 205. The angled surface distal to the proximal end may provide an additional cleaning surface 213.

Figure 10A:
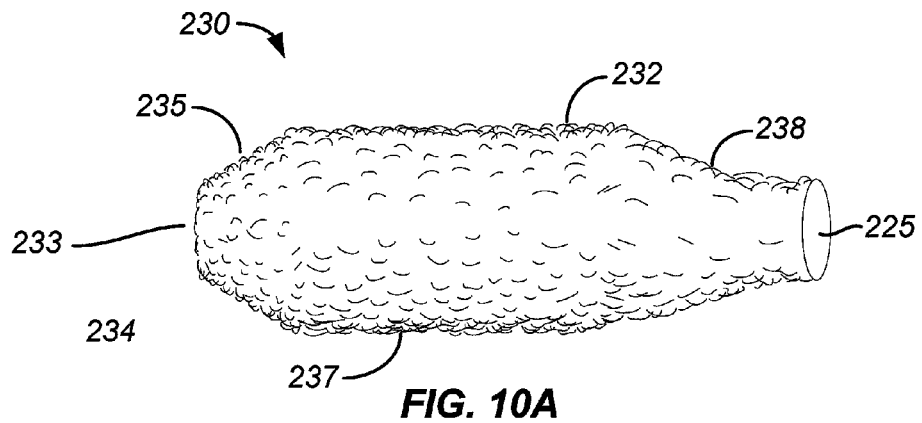
FIGS. 10A, 10B and 10C illustrate alternative cleaning device embodiments.
Figure 10B:
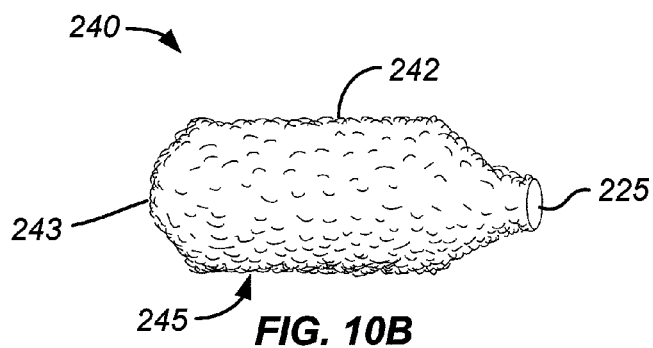
Figure 10C:
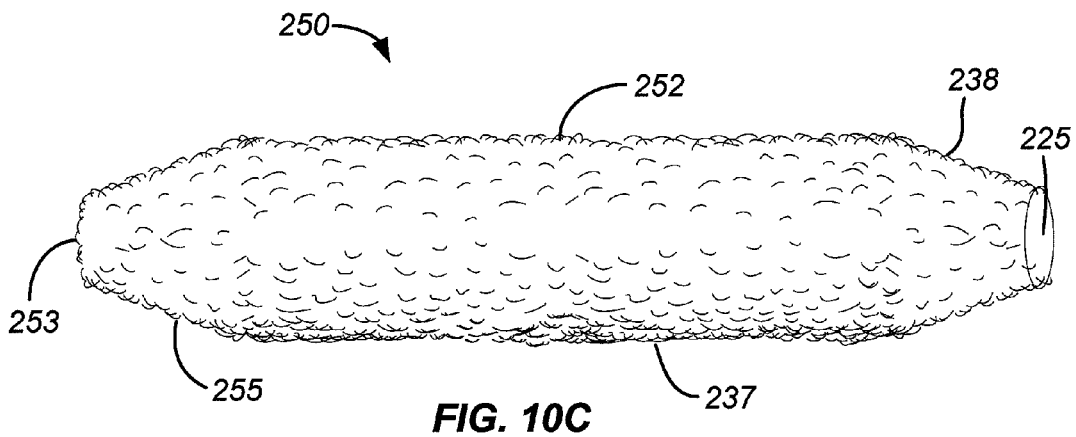

FIGS. 10A, 10B and 10C illustrate alternative cleaning device embodiments. FIG. 10A illustrates a cleaning device 230 having a distal cleaning surface 233 including a distal edge 234. The angled cleaning surface 235 proximal to the distal end is less defined than the similar cleaning surface 209 illustrated in the cleaning device 200 of FIG. 9C. Similarly, the angled surface 238 distal to the proximal end is also less defined than the similar cleaning surface 213 illustrated in the cleaning device 200 of FIG. 9C. The cleaning device 230 also includes a longitudinal cleaning surface 237.

FIG. 10B illustrates a cleaning device 240 having a short, blunt body 242. Additionally, the cleaning device 240 has a distal cleaning surface 243 formed by the blunt distal tip of the device. The cleaning device 240 also includes a longitudinal cleaning surface 245.

FIG. 10C illustrates a cleaning device 250 similar to the cleaning device 200. The cleaning device to 50 includes a body 252 shapes to have a rounded tip cleaning surface 253, a distal end cleaning surface 255, a longitudinal cleaning surface 237 and a proximal cleaning surface 238. The cleaning device 250 differs from the cleaning device 200 and in that none of the cleaning surfaces on the cleaning device 250 contain any edges common to the cleaning surfaces of cleaning device 200. Instead, the cleaning device 250 has an elongated shape similar to the cleaning device 200 without the edges. The cleaning surfaces of the cleaning device 250 are less distinct, not well defined and blend one into the next as illustrated in FIG. 10C.

Figure 11A:
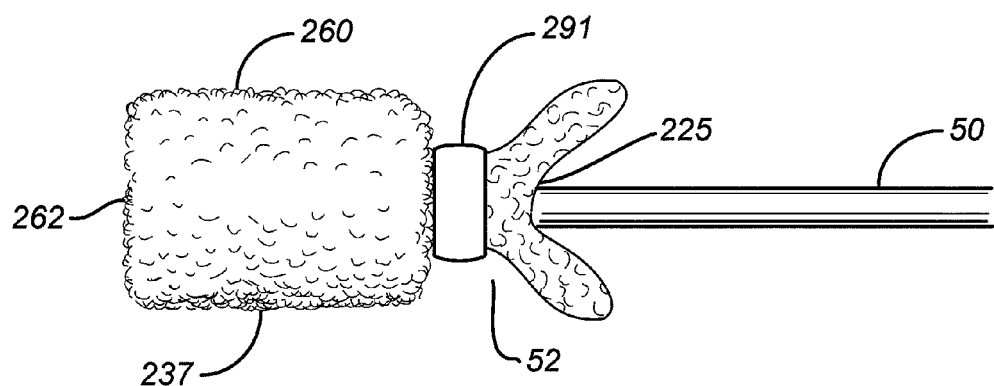
FIGS. 11A and 11B illustrate a technique to secure a cleaning device to an instrument.
Figure 11B:
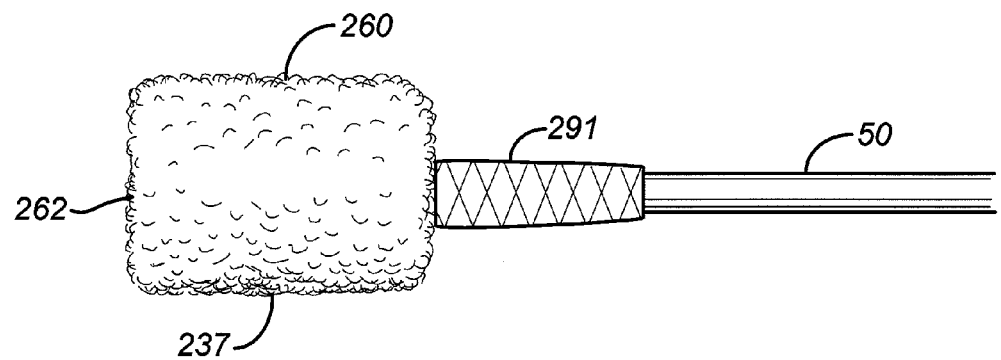

The cleaning device may be affixed to an instrument using any suitable technique. FIGS. 11A and 11B illustrate one technique to secure a cleaning device to an instrument 50. The cleaning device 260 includes a distal cleaning surface 262, a longitudinal cleaning surface 237 and a distal opening 225 sized to fit the instrument 50. As best seen in FIG. 11A, the cleaning device 260 is positioned onto the instrument distal end 52 with an elastic sleeve 291 positioned distal to the cleaning device proximal end. The cleaning device 260 is secured to the instrument 50 by unrolling the elastic sleeve 291 as shown in FIG. 11B.

Figure 12:
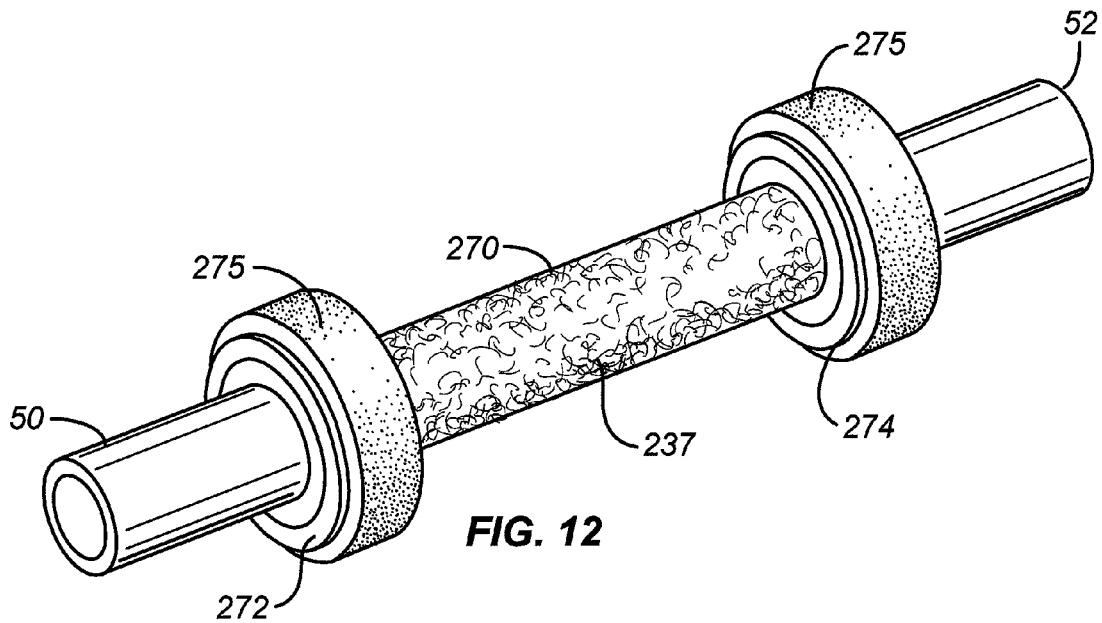
FIG. 12 illustrates the use of an adhesive on the ends of a cleaning device to secure the cleaning device to an instrument.

Alternatively, an adhesive may be used to affix a cleaning device to an instrument. FIG. 12 illustrates a cleaning device 270 with a rolled proximal end 272 and rolled distal end 274. The exposed portion of the rolled ends contacts the instrument outer surface when unrolled. A suitable adhesive 275 is applied to the exposed surface as best seen in FIG. 12. When the rolled ends 272, 274 are unrolled, the adhesive 275 secures the cleaning device 270 to the instrument 50.

Figure 13A:
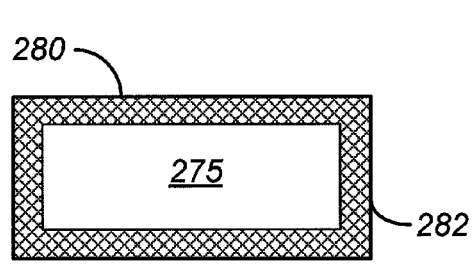
FIG. 13A illustrates a cleaning device in the form of a sheet with an adhesive backing.
Figure 13B:
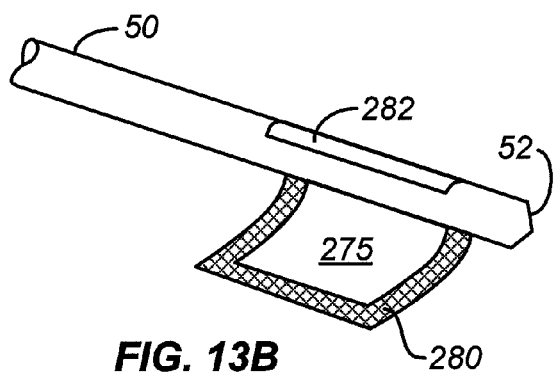
FIG. 13B illustrates the cleaning device of FIG. 13A being applied to an instrument.

The cleaning device need not limited to elongate, cylindrical, or rounded structures. A cleaning device may take any of a variety of shapes. For example, a cleaning device they be a rectangular sheet. FIG. 13A illustrates a cleaning device 280 in the form of a rectangular sheet with an adhesive backing 275. The cleaning device 280 may be formed from an abrasive material or the sheet may be formed from a suitable base material with an abrasive surface or abrasive elements attached thereto. FIG. 13B illustrates the cleaning device 280 of FIG. 13A being applied using the adhesive backing 275 to a position proximal to the instrument distal end 52.

Figure 14:
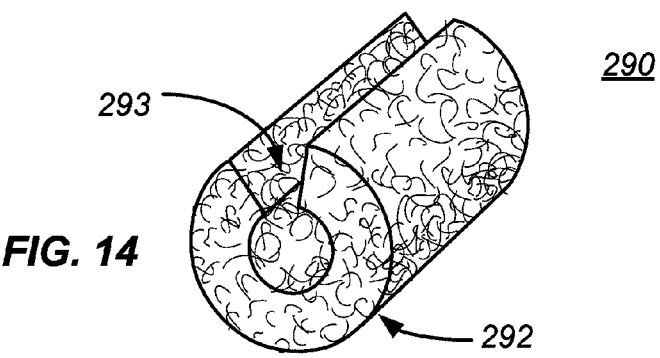
FIG. 14 is a perspective view of a cleaning device with a slot to allow attachment to an instrument.

In other embodiments, the cleaning device may be shaped to conform to or attach to the outer surface of the instrument 50. Conforming to the outer surface of the instrument 50 includes conforming to the entire outer surface or only a portion of the outer surface. FIG. 14 is a perspective view of a cleaning device 290 with a c-shaped body 292 having a longitudinal slot 293 to allow attachment to an instrument 50. The cleaning device 290 would partially conform to a suitably sized cylindrical instrument, such as an endoscope for example. The slot 293 allows the cleaning device 290 to snap onto the instrument 50 at any desired position on the instrument (see FIGS. 8A and 8B).

A cleaning surface may also include all or a portion of the outer surface of a cleaning device. The outer surface includes the gross shape of that surface, such as a cylindrical shape for example. The outer surface may also include features on that outer surface such as edges, frames or loops. While the descriptions above for FIGS. 9-14 may refer to edges, sides, or portions of a particular shape of cleaning device, the cleaning surface may also include the cleaning device in its entirety.

Figure 15:
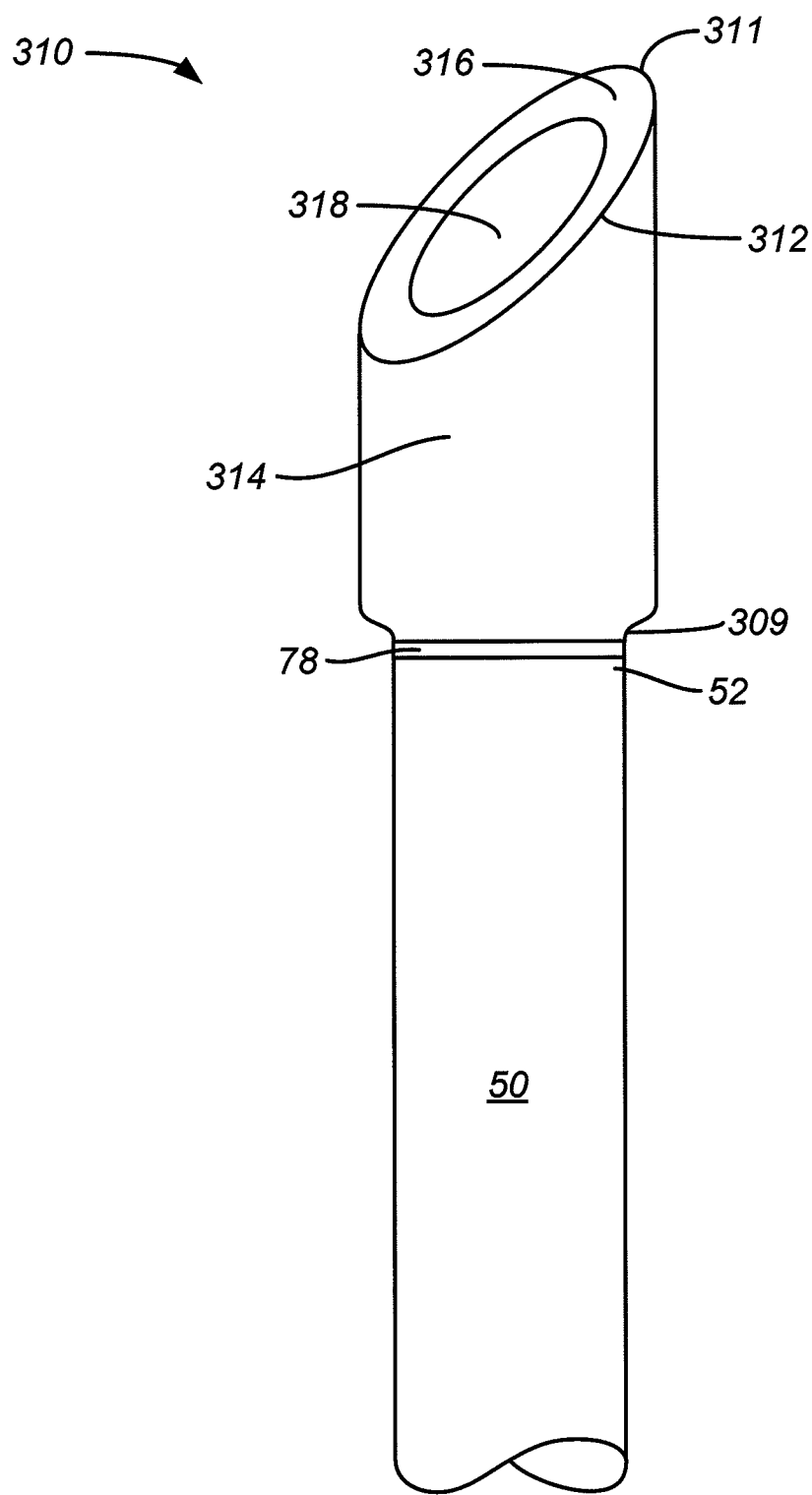
FIG. 15 is a perspective view of a cleaning device positioned on the distal end of an instrument.

FIG. 15 is a perspective view of a cleaning device 310 positioned on the instrument distal end 52. Optionally, a joint or attachment 78 secures the cleaning device 310 to the instrument distal end 52. Alternatively, the cleaning device 310 and the instrument 50 are a single unitary device. The cleaning device 310 includes a distal end 311, a proximal end 309 and an opening 318. The cleaning device 310 includes a number of cleaning surfaces. A portion of the cleaning surface 316 is positioned proximal to the distal end of the cleaning device 311. The cleaning surfaces include, at least, the edge 312, the top surface 316 and outer surface 314. In one embodiment, the cleaning device 310 is a plastic endoscopic mucosal resection cap.

Figure 16:
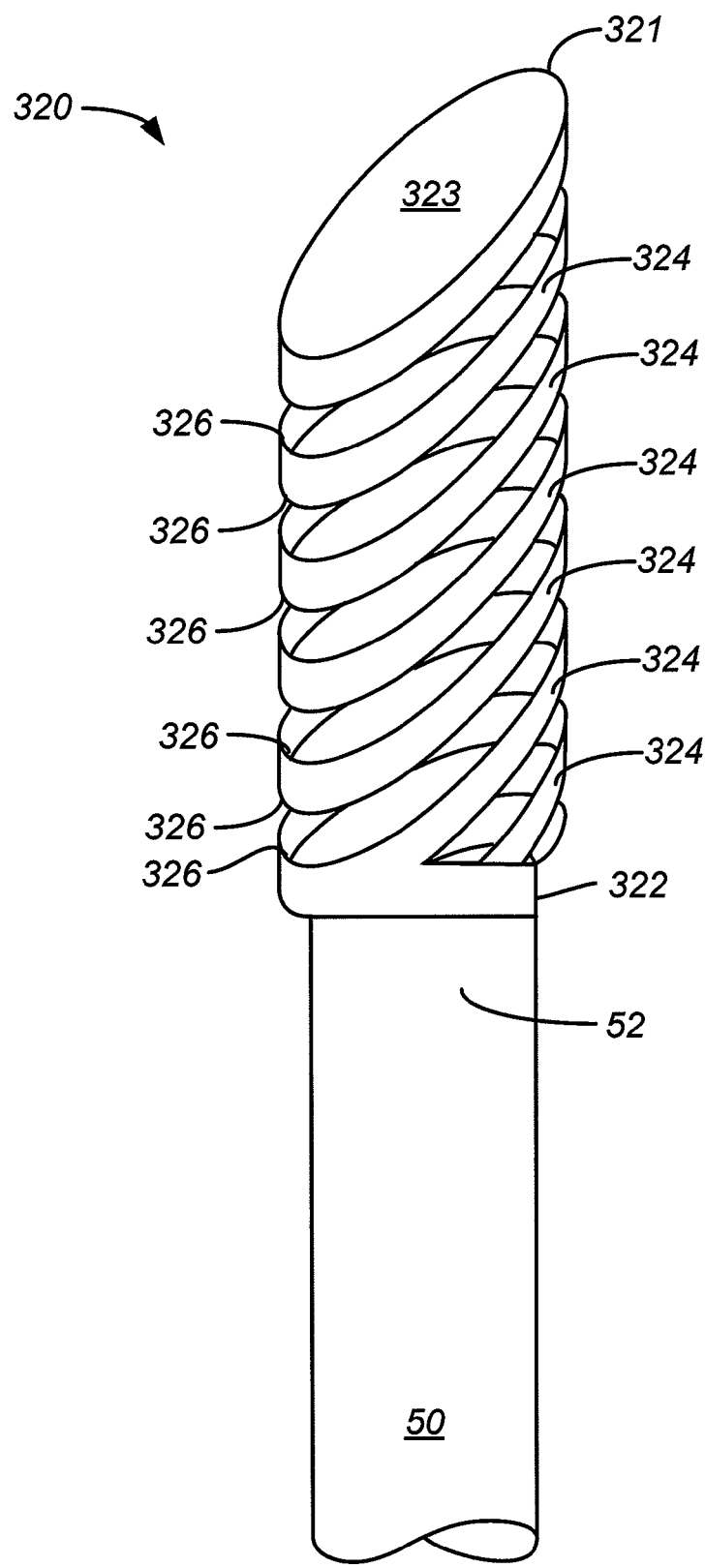
FIG. 16 is a perspective view of a cleaning device positioned on the distal end of an instrument.

FIG. 16 is a perspective view of a cleaning device 320 positioned on the distal end 52 of an instrument 50. The cleaning device 320 includes a distal end 321 and a proximal end 322. The cleaning device 320 includes a distal angled cleaning surface 323. The cleaning device 320 may be formed from a single spiral band or, alternatively, from a plurality of single rings or bands joined together. In one aspect, FIG. 16 illustrates an edge, here either distal end 321 or angled surface 323, that is supported by one or more of a frame, a ridge or a ring. The spiral shaped bends 324 may also be cut from a tube using techniques similar to those used in the fabrication of stents.

The use of single or multiple bands produced a large number of cleaning surfaces. One cleaning surface is the spiral ring outside surface 324. Another cleaning surface is an edge 326 of the spiral ring. The cleaning surfaces on the cleaning device 320 may be smooth and as illustrated or textured to improve cleaning efficiency.

Cleaning device 320 also illustrates one embodiment of the cleaning device having a cleaning surface such as the distal and 321 and another cleaning surface that is non-continuous with a distal and 321 such as the angled surface 323. Similarly, either the distal and 321 or the angled surface 323 are non-continuous cleaning surfaces with regard to the bend cleaning surfaces 324. In another alternative, all or a portion of the spiral ring could be used to at least partially extend about the instrument.

FIG. 17 is a perspective view of a cleaning device 330 positioned to on the instrument distal end 52. Like the cleaning device of FIG. 16, the cleaning device 330 includes a longitudinally arranged ring 331 with a number of cleaning surfaces. Cleaning surfaces of the ring 331 include edges 334 and surfaces 332. In one aspect, the device 330 is attached to the instrument 50 at both ends. When the distal end of the instrument 50 is straight as illustrated, the ring 331 remains generally aligned along the longitudinal axis of the instrument 50. Because the device 330 is not attached along its length, flexing or bending the instrument distal end 52 causes the ring 331 to flex causing the edges 334 to fan outward to produce a multi-edge scraping structure. The device 330 also illustrates another example of an edge that is supported by one or more of a frame, a ridge or a ring.

FIGS. 18A and 18B are perspective and end views, respectively, of a cleaning device 340 positioned on the instrument distal end 52. The distal end cleaning device 340 includes two cone shaped scrapers namely an outer cone 341 and an inner cone 342. The proximal end 343 of device 340 is adapted to fit onto the instrument 50. The cone scrapers 341, 342 are arranged about the instrument 50 with distal facing openings. Cone 341 terminates in an edge 344. Cone 342 terminates in an edge 345. In other embodiments, the onces 341 and 342 may terminate in multiple edges, textured edges, or combinations thereof. A recess 346 exists between the inner surface of cone 341 and outer surface of cone 342. Recess 346 allows for an area to retain debris produced as a result of cleaning.

FIGS. 19A and 19B are perspective and end views, respectively, of a cleaning device 350 positioned on the instrument distal end 52. The distal end cleaning device 350 includes three cone shaped scrapers namely an outer cone 341, an inner cone 342 and an end cone 347. The proximal end 343 of device 350 is adapted to fit onto the instrument 50. The cone scrapers 341, 342 and 347 are arranged about the instrument 50 with distal facing openings. Cone 341 terminates in an edge 344. Cone 342 terminates in an edge 345. Cone 347 terminates in an edge 348. In other embodiments, the cones 341, 342 and 347 may terminate in multiple edges, textured edges, or combinations thereof. A recess 346 exists between the inner surface of cone 341 and outer surface of cone 342. Recess 346 allows for an area to retain debris produced as a result of cleaning. Similarly, a recess 349 exists between the end cone 347 and the inner cone 342.

FIGS. 18A, 18B, 19A, and 19B illustrate scrapers with a truncated conical shape and a circular distal opening. Other shapes and configurations are possible. The distal openings may have an elliptical, oblong, or other non-circular shapes. In the illustrated embodiments, the cones are concentrically arranged relative to one another or to the instrument 50. Other arrangements are possible. For example, the cones may be arranged eccentrically about the instrument 50.

Moreover, while the previous embodiments illustrate cleaning surfaces that are cones arranged about an instrument, other cleaning surface configurations are possible. For example, a single flap may be used. FIGS. 20A and 20B are perspective and end views, respectively, of a cleaning device 360 positioned on the instrument distal end 52. The cleaning device 360 includes a body 361 and a proximal end 363 configured to engage with or remain on the instrument 50. A single flap 362 extends from the body 361. The flap 362 terminates in a distal edge 344. The flap distal edge 344 extends beyond the instrument distal end 52. The flap 344 also includes a longitudinal edge 366 and a proximal edge 367. As illustrated, the distal edge 344, longitudinal 366 and proximal edges 367 are smooth. In other embodiments, the flap edges may terminate in multiple edges, textured edges, or combinations thereof. As best seen in FIG. 20B, the flap 362 is arranged about the top portion of the instrument 50.

FIGS. 21A and 21B are perspective and end views, respectively of another cleaning device positioned on the distal end of an instrument having a single flap cleaning surface. The cleaning device 370 includes a body 371 with a proximal and 373 configured to engage with or remain on the instrument 50. A single flap 372 extends from the body 371 beyond the instrument distal end 52. The flap 372 terminates in a distal edge 344. The flap distal edge 344 extends beyond the instrument distal end 52. The flap 372 also includes edge 366 and a tapered longitudinal edge 377. As illustrated, the distal edge 344, tapered longitudinal edge 377 and edge 366 are smooth. In other embodiments, each edge may include multiple edges, be textured, be subjected to surface treatment, or combinations thereof. As best seen in FIG. 21B, the flap 372 is arranged about the top portion of the instrument 50.

FIGS. 22A and 22B are perspective and end views, respectively, of a multiple flap cleaning device 380 positioned on the distal end of an instrument. The cleaning device 380 includes a body 381 and a proximal end 383 configured to engage with or remain on the instrument 50. Three flaps to 62, 382, and 384 extend distally from the body 381. The flap 362, described above in FIG. 21B, terminates in a distal edge 344. The flap 362 distal edge 344 extends beyond the instrument distal end 52. The flap 362 also includes a tapered longitudinal edge and a proximal edge as described above. The flap 382 terminates in a distal edge 344. The flap 382 distal edge 344 extends beyond and above the instrument distal end 52. The flap 382 also includes a tapered longitudinal edge and a proximal edge. The flap 384 terminates in a distal edge 344. The flap 384 distal edge 344 extends beyond and above the instrument distal end 52. The flap 384 also includes a tapered longitudinal edge and a proximal edge. The illustrated edges 344 are smooth. In other embodiments, the flap edges 344 may terminate in multiple edges similar to windshield wiper blades, be textured or roughened, or combinations thereof. As best seen in FIG. 22B, the flaps 362, 382 and 384 are arranged about the instrument distal end 52.

While illustrated as having a proximal end larger than the diameter of the instrument 50, in other embodiments of the cleaning devices in FIGS. 20A-22B, the proximal end of the device is the same diameter so as to form a friction fit on the instrument 50 as illustrated in FIGS. 18A and 19A.

FIG. 23 is a perspective view of a cleaning device 390 positioned on the instrument distal end 52. The cleaning device 390 includes a plurality of cleaning surfaces including surfaces 392 and edges 394. Recesses 396 are formed where an edge 394 extends over a surface 392. The cleaning device 390 may be formed from organic or non-organic polymers whereby the stiffness of the edges controlled by both material selection and dimension, is adequate to achieve scrapping. While illustrated as smooth, the surfaces 392 and edges 394 of the cleaning device 390 may be textured, roughened, or include surface features to increase the cleaning efficiency.

FIG. 24 is a perspective view of a cleaning device 400 positioned on the distal end of an instrument 50. The cleaning device 400 includes a body 402 on the distal end of an instrument. A flap 360, described above in FIG. 20A, is attached to the body 402 and extends beyond the instrument distal end 52. A ring 404 is attached to the body 402 proximal to the flap 360. The ring 404 includes cleaning surfaces in the form of surface 405 and edes 406. The body 402 may be solid, semi-solid, or a balloon or other inflatable structure. While illustrated as smooth, the surfaces and edges of the cleaning device 400 may be textured, roughened, or include surface features to increase the cleaning efficiency.

The device is illustrated in FIGS. 18-24, in addition to other embodiments, illustrate cleaning devices where the cleaning device has a proximal end and a distal end and the proximal end has a circumference that nearly matches the circumference of the instrument and the distal end has a circumference larger than the instrument. Additionally, the various scrapers, edges and cleaning surfaces illustrated in the various embodiments provide numerous examples of cleaning surfaces that are non-continuous with other cleaning surfaces on the same cleaning device.

In an embodiment where the body is inflatable, the ring 404 and the portion of the flap 360 extending around the body 402 are expandable along with the inflatable body. The use of an inflatable cleaning device body 402 allows the cleaning device 400 to advance to the treatment site in a reduced diameter size (i.e., deflated). Once positioned at the treatment site, the body 402 is inflated in order to place the cleaning surfaces of the device 400 into contact with tissue at the treatment site.

Figure 25:
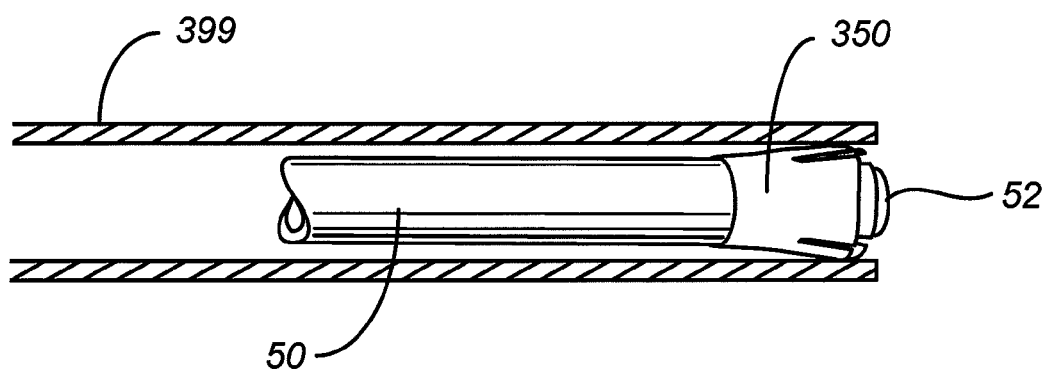
FIG. 25 illustrates a cleaning device in a stowed configuration within a sheath.

In addition to using inflatable cleaning devices, other techniques are possible to reduce the diameter of the cleaning device for advancement to a treatment site. For example, FIG. 25 illustrates a cleaning device 350 (described above in FIG. 19A) in a stowed configuration within a sheath 399. The sheath 399 is positioned around at least a portion of the cleaning device. Inside of the sheath 399, the flaps 342 are held against the outer surface of the instrument 50 thereby reducing the overall diameter of the cleaning device. As such, cleaning device 350 illustrates an example of a cleaning device movable between a stowed condition adjacent the instrument and a deployed condition for engaging tissue on the lumen. Additionally, the cleaning device 350, along with other embodiments described herein, illustrate a cleaning device diameter in a stowed condition that is less than the diameter of the cleaning device in the deployed condition. In this way, a cleaning device may remain in a stowed condition during movement to a treatment site. Once positioned at the treatment site, the sheath 399 is withdrawn and the flaps 342 expand out into the open configuration illustrated in FIG. 19A. While described with reference to the cleaning device of FIG. 19A, a sheath may be used to reduce the diameter or render a stowed configuration to any cleaning device embodiment described herein.

Figure 26A:
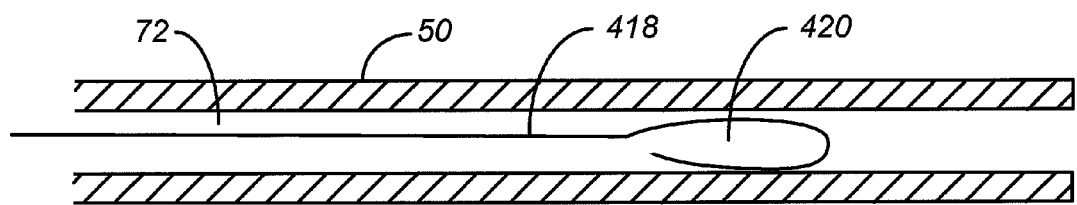
FIG. 26A illustrates a cleaning device within a cavity in an instrument.

FIG. 26A illustrates a cleaning device 420 within a cavity 72 in an instrument 50. The cleaning device 420 includes an expandable hoop or ring mounted on a shaft 418. In the illustrated embodiment, the hoop is open and when extended out of the cavity 72 will expand into contact with the surrounding tissue. Alternatively, the hoop may be closed loop with a fixed diameter selected for a particular treatment site. The cavity 72 may be a dedicated port in the instrument 50 for storing the cleaning device 420. The cavity 72 may also be the working channel of an endoscope. While the cavity 72 is illustrated in use with a hoop style cleaning device, is to be appreciated that either or both of the cavity and cleaning device may be modified to allow any cleaning device described herein to be deployed from a cavity or working channel of an instrument.

Figure 26B:
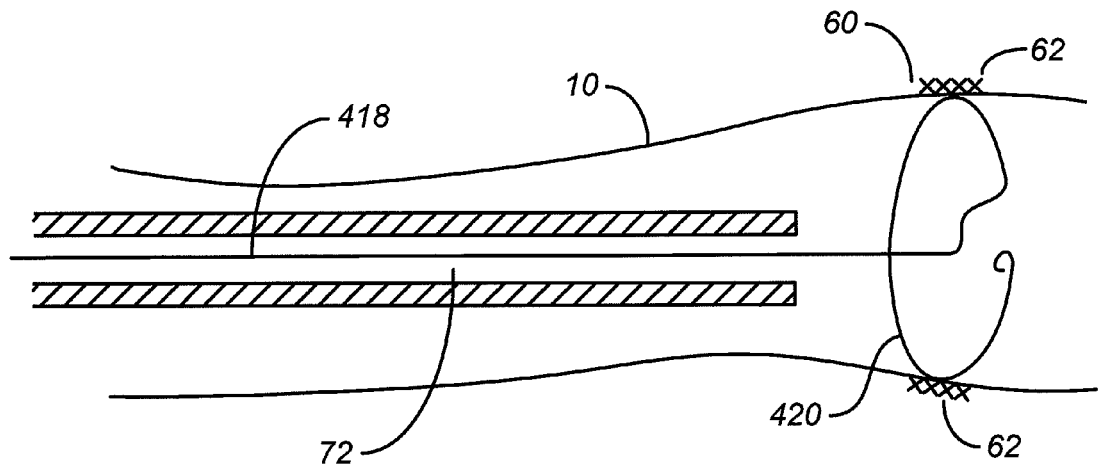
FIG. 26B illustrates the cleaning device of FIG. 26A in use to remove tissue.

FIG. 26B illustrates the cleaning device of FIG. 26A in use to remove tissue. As illustrated, the cleaning device 420 has exited the cavity 72 and expanded into contact with the tissue at a treatment site 60. FIG. 26B also provides another example where in the diameter of the cleaning device in the stowed condition (FIG. 26A) is less than the diameter of the cleaning device in the deployed condition.

As used herein, and edge on a cleaning device may be a blunt edge. A blunt edge is an edge on a cleaning device or a cleaning surface having a shape, contour, texture or other form suited to the removal of debris by rubbing, scraping or abrasion. As such, a portion of a cleaning device may comprise a blunt edge. Moreover, the blunt edge may be supported by one or more of a frame, a ridge or a ring as illustrated and described herein. Generally, during typical use, a blunt edge as described herein will not lacerate tissue at a treatment site.

While the above description relates to the use of cleaning devices of the inventions during ablation treatments, the device and methods of the invention are not so limited. Other alternative uses of the cleaning devices are possible. For example, a cleaning device may be used to clean, wipe or otherwise remove debris such as, but not limited to, food, mucus, blood, or alimentary tract by-products such as bile, feces and the like from the alimentary tract. Removal of this debris may enhance visualization of the organ to aid in performing a diagnosis or evaluation. By removing debris as a result of using a cleaning device or method described herein, a physician or health care provider may be better able to determine the location of bleeding, evaluate or analyze tissue type, identify and/or localize a perforation or prepare an organ for a subsequent therapeutic or diagnostic treatment (e.g., biopsy, ablation, banding and the like.)

Additionally, embodiments of the cleaning devices and methods described herein may be used to produce hemostasis of alimentary treat bleeds. Utilizing the devices and methods described herein for tamponade, it is believed that temporary or permanent hemostasis could be achieved. To assist in permanent hemostasis, the device may be coated with a material to assist in thrombosis such as thrombin, fibrin, collagen or other suitable coatings or pharmacological agents. Additionally or alternatively, the cleaning device may be formed from thrombin, fibrin or collagen or coated by partially or completely by these or similar materials. Additionally, the characteristics of the cleaning device such as the roughness, porosity, absorption qualities such as a hydrophilic material, material selection, and/or suitable conventional material pre-treatment may be used to adapt the device for particular applications such as for cleaning, hemostatis or for other applications.

While numerous embodiments of the present invention have been shown and described herein, it is to be appreciated by those of skill in the art that such embodiments are provided by way of example only. Numerous variations, changes, and substitution will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. An apparatus for treating tissue within a lumen of the alimentary system, comprising:
   an ablation device configured to couple with a distal end of a therapeutic or diagnostic instrument, the ablation device comprising:
      a base configured to couple with an outer surface of the distal end of the therapeutic or diagnostic instrument;
      a longitudinal support configured to support one or more electrical ablation structures that are coupled with the longitudinal support; and
      a rotational support pivotably coupling the base directly with the longitudinal support, the rotational support configured to permit the longitudinal support to pivot with respect to the base; and
   a cleaning device configured to be supported by the therapeutic or diagnostic instrument and positioned proximal to the ablation device, the cleaning device having a portion of a cleaning surface positioned proximal to the distal end of the instrument, wherein the cleaning device is configured to clean tissue treated by the ablation device.

2. The apparatus of claim 1, wherein the cleaning device comprises a porous material.

3. The apparatus of claim 2, wherein the porous material comprises open cells.

4. The apparatus of claim 1, wherein a portion of the cleaning device comprises a blunt edge.

5. The apparatus of claim 4, wherein the blunt edge is supported by one or more of a frame, a ridge, or a ring.

6. The apparatus of claim 1, wherein the cleaning device is shaped to mount onto the therapeutic or diagnostic instrument.

7. The apparatus of claim 1, wherein the cleaning device comprises an adhesive surface used to secure the cleaning device to the therapeutic or diagnostic instrument.

8. The apparatus of claim 1, further comprising a sheath around at least portion of the cleaning device.

9. The apparatus of claim 1, further comprising a cavity in the therapeutic or diagnostic instrument for storing the cleaning device.

10. The apparatus of claim 1, wherein the therapeutic or diagnostic instrument is an endoscope.

11. The apparatus of claim 1, wherein the cleaning device is further configured to remain in a stowed condition during movement to a treatment site.

12. The apparatus of claim 1, wherein the cleaning device is further configured to be movable between a stowed condition adjacent the therapeutic or diagnostic instrument and a deployed condition for engaging tissue of the lumen.

13. The apparatus of claim 12, wherein a diameter of the cleaning device in the stowed condition is less than a diameter of the cleaning device in the deployed condition.

14. The apparatus of claim 1, wherein the cleaning device is formed from a compressible material.

15. The apparatus of claim 1, wherein the cleaning device is configured to be releasably joined to the exterior surface of the therapeutic or diagnostic instrument.

16. The apparatus of claim 1, wherein the cleaning device is shaped to conform to the outer surface of a portion of the therapeutic or diagnostic instrument.

17. The apparatus of claim 1, further comprising a cavity in the cleaning device for storing a portion of the tissue from the lumen.

18. The apparatus of claim 17, wherein the cavity is a pore of the cleaning device.

19. The apparatus of claim 1, wherein the cleaning device comprises a slot sized to fit over the therapeutic or diagnostic instrument.

* * * * *